United States Patent
von Blücher et al.

(10) Patent No.: US 10,426,670 B2
(45) Date of Patent: *Oct. 1, 2019

(54) WOUND DRESSING WITH AN AIR PERMEABLE LAYER

(75) Inventors: Hasso von Blücher, Erkrath (DE); Raik Schönfeld, Hannover (DE); Frank Pallaske, Gersdorf (DE)

(73) Assignee: Blücher GmbH, Erkrath (DE)

( * ) Notice: Subject to any disclaimer, the term of this patent is extended or adjusted under 35 U.S.C. 154(b) by 1197 days.
This patent is subject to a terminal disclaimer.

(21) Appl. No.: 14/342,466

(22) PCT Filed: Aug. 31, 2012

(86) PCT No.: PCT/EP2012/003661
§ 371 (c)(1),
(2), (4) Date: Jul. 17, 2014

(87) PCT Pub. No.: WO2013/029798
PCT Pub. Date: Mar. 7, 2013

(65) Prior Publication Data
US 2015/0094672 A1    Apr. 2, 2015

(30) Foreign Application Priority Data

Sep. 2, 2011 (DE) .......... 10 2011 112 094
Dec. 8, 2011 (DE) .......... 10 2011 120 492

(51) Int. Cl.
| | |
|---|---|
| A61F 13/15 | (2006.01) |
| A61F 13/20 | (2006.01) |
| A61F 13/00 | (2006.01) |
| A61L 15/32 | (2006.01) |
| A61L 15/42 | (2006.01) |

(Continued)

(52) U.S. Cl.
CPC .. *A61F 13/00068* (2013.01); *A61F 13/00012* (2013.01); *A61F 13/00046* (2013.01); *A61F 13/00063* (2013.01); *A61L 15/18* (2013.01); *A61L 15/325* (2013.01); *A61L 15/42* (2013.01);
(Continued)

(58) Field of Classification Search
CPC ............. A61F 13/00; A61F 13/00008; A61F 13/00029; A61F 13/00038; A61F 13/00046; A61F 2013/00089
See application file for complete search history.

(56) References Cited

U.S. PATENT DOCUMENTS 3,767,784 A * 10/1973 Gluck ............... A61F 13/00063
424/445
4,341,207 A * 7/1982 Steer .................. A61L 15/18
602/47

(Continued)

FOREIGN PATENT DOCUMENTS

| CN | 1867364 A | 11/2006 |
|---|---|---|
| CN | 201179150 Y | 1/2009 |

(Continued)

*Primary Examiner* — Michelle M Kidwell
(74) *Attorney, Agent, or Firm* — Edward E. Sowers; Brannon Sowers & Cracraft PC

(57) ABSTRACT

The invention relates to a wound dressing which is particularly suited for therapeutically dressing wounds. Said wound dressing comprises at least one air permeable layer having a porous and/or foam-based structure, particularly in the form of a solid foam ("foam layer"), and at least one sorbent in the form of activated carbon.

3 Claims, 1 Drawing Sheet

(51) Int. Cl.
*A61L 15/44* (2006.01)
*A61L 15/18* (2006.01)

(52) U.S. Cl.
CPC ............. *A61L 15/425* (2013.01); *A61L 15/44* (2013.01); *A61L 2300/108* (2013.01)

(56) References Cited

U.S. PATENT DOCUMENTS

| | | | |
|---|---|---|---|
| 4,538,603 A * | 9/1985 | Pawelchak | A61L 15/18 424/447 |
| 5,925,009 A * | 7/1999 | Mahoney | A61L 15/18 602/44 |
| 5,973,221 A | 10/1999 | Collyer et al. | |
| 6,399,091 B1 * | 6/2002 | Berthold | A61M 31/002 424/443 |
| 7,737,083 B2 * | 6/2010 | von Blucher | A61K 33/44 502/416 |
| 9,474,827 B2 * | 10/2016 | Blucher | A61L 15/18 |
| 2004/0241215 A1 * | 12/2004 | Lipman | A61F 13/0246 424/445 |
| 2005/0251082 A1 | 11/2005 | Del Bono | |
| 2006/0159731 A1 * | 7/2006 | Shoshan | A61K 38/39 424/443 |
| 2009/0263468 A1 * | 10/2009 | McAnulty | A61K 47/42 424/443 |
| 2012/0003456 A1 * | 1/2012 | Marchgraber | C08J 9/0061 428/219 |
| 2015/0104496 A1 | 4/2015 | Riesinger | |

FOREIGN PATENT DOCUMENTS

| | | | | |
|---|---|---|---|---|
| DE | 3302984 A1 | 8/1984 | | |
| DE | 102007030931 A1 | 1/2009 | | |
| EP | 0053936 A2 | 6/1982 | | |
| EP | 0 099 758 | * | 2/1984 | ............ A61F 13/00 |
| EP | 0117438 A2 | 9/1984 | | |
| JP | S57119738 A | 7/1982 | | |
| JP | 2001-520274 A | 10/2001 | | |
| WO | 8605970 A1 | 10/1986 | | |
| WO | 9920318 A2 | 4/1999 | | |

\* cited by examiner

WOUND DRESSING WITH AN AIR PERMEABLE LAYER

CROSS-REFERENCES TO RELATED APPLICATIONS

This application is a National Stage filing of International Application PCT/EP 2012/003661, filed Aug. 31, 2012, claiming priority to German Applications No. DE 10 2011 112 094.0 filed Sep. 2, 2011, and DE 10 2011 120 492.3 filed Dec. 8, 2011, entitled "WOUND DRESSING WITH AN AIR PERMEABLE LAYER". The subject application claims priority to PCT/EP 2012/003661, and to German Applications No. DE 2011 112 094.0 and DE 10 2011 120 492.3 and incorporates all by reference herein, in their entirety.

BACKGROUND OF THE INVENTION

The present invention relates to the medical field of wound care or wound healing, in particular based on local application of a wound dressing.

In particular, the present invention relates to a wound dressing which is preferably suitable for therapeutic wound care of the human or animal body.

The present invention further relates to use of the wound dressing according to the invention for therapeutic wound care.

According to medical definition and in the context of the present invention, a wound is understood to mean a break in the continuity of body tissues with or without substance loss, such a break in general being caused by mechanical injuries or physically caused cell damage.

Wounds are classified into various types depending on their causes. Thus wounds created by external trauma are classed as mechanical wounds, these mainly being cutting and piercing wounds, crushing, laceration, scratch and abrasion wounds. Another form of wounds is described as thermal wounds, which are caused by the action of extreme heat or cold. In contrast, chemical wounds are caused by the action of chemicals, in particular by erosion by acids or alkalis. Tissue breaks or damage which arise under the action of actinic radiation, e.g. ultraviolet radiation and/or ionizing radiation, are described as radiation wounds.

In addition, depending on the physiological condition, a distinction is also made between necrotizing, infected and/or chronic or acute wounds.

For further details on the term "wound", reference can be made to Pschyrembel—Clinical Dictionary, 257$^{th}$ edition, 1994, Verlag de Gruyter, Berlin/New York, page 1679, keyword "wound", the content whereof relating to this is by reference completely included herein.

Wound healing, i.e. the physiological processes for the regeneration of the destroyed tissue and for closure of the wound, takes place in particular by regeneration of connective tissue and capillaries for the circulation, during which in general three phases are passed through. This process can extend over a period of up to four weeks or longer depending on the size and depth of the wound.

In the first phase, also described as latency or inflammatory phase, within the first hours after wounding has occurred, firstly exudation of body fluids takes place, in particular of blood, to free the wound opening from foreign bodies, germs and dead tissue. Next, a scab, which protects the wound externally from the penetration of germs and foreign bodies is formed through clotting of the blood that has emerged. After the formation of the scab, the resorption phase of the latency phase begins, in which a catabolic autolysis also takes place, i.e. macrophages migrate into the wound tissue and phagocytize the coagulated blood in the wound opening. Foreign bodies or microorganisms which may have penetrated are degraded in this phase, which can be associated with mild to moderate inflammatory symptoms. Further, in the resorption phase the build-up of the basal epithelium and of granulation tissue begins. After about one to three days after causation of the wound, the latency phase is generally completed and the latency phase passes into the second phase, the so-called proliferation or granulation phase, which in general lasts from the fourth to the seventh day after the injury. During this, the anabolic repair, which in particular refers to the formation of collagen by fibroblasts, begins. In the repair or epithelization phase, which begins from about the eighth day after the occurrence of the wound, final scar tissue is formed and the squamous epithelium of the skin is renewed. The scar tissue formed has neither sebaceous nor sweat glands and appears white to mother-of-pearl on the skin. In contrast to undamaged tissue, the collagen in the scar tissue is no longer complexly linked, but instead aligned parallel.

For further information on the term "wound healing", reference can be made to Pschyrembel—Clinical Dictionary, 257$^{th}$ edition, 1994, Verlag de Gruyter, Berlin/New York, page 1670, keyword "wound healing", the content whereof relating to this is by reference completely included herein.

In the prior art, many medical articles and objects and therapeutic measures are known which serve to support or accelerate wound healing. Nevertheless, complications or impeded healing often occur, in particular when the wound is very extensive or many tissue layers are affected.

A relatively commonly occurring complication in wound healing are wound infections triggered by bacteria, fungi or viruses, which are attributable in particular to defective wound hygiene or increased occurrence of germs, such as is often the case in hospitals. Through contamination with various microorganisms, in particular bacterial infections of the wound can occur, during which because of the infection classical signs of local inflammation arise, such as pain, swelling, reddening and overheating. In the worst case, however, as a result of phlegmonous, i.e. extensive, dissemination, a general infection or life-threatening sepsis can occur with high fever and chills. In the causation of wound infections, the so-called hospital germs, such as *Proteus mirabilis, Pseudomonas aeruginosa, Staphylococcus epidermidis, Staphylococcus aureus* and *Escherichia coli* play a significant part. A particular problem with such infections with hospital germs are the many antibiotic resistances acquired by the strains concerned in the course of time, as a result of which infections arising can only be treated with extreme difficulty, above all in patients with an already weakened immune system. Numerous strains exist of *Staphylococcus aureus* in particular which have resistance to all beta-lactam antibiotics obtainable on the market, such as methicillin and oxacillin, and various other antibiotic classes such as glycopeptide antibiotics, sulfonamides, quinolones or tetracyclines. Consequently, in case of infections with such germs a therapy independent of the administration of antibiotics must be given to avoid systemic dissemination of the pathogen in the body. However there is still a serious lack of such therapeutic concepts in the state of the art, so that the death rate due to multiresistant hospital germs exceeds the mortality rate due to seasonal influenza.

A further problem in wound healing can be the formation of necroses, during which the pathological death of cells on the living body takes place. In the case of necroses, successful therapy mostly necessitates a debridement, which means the excision of the dead tissue and serves for stimulation of wound healing and avoidance of dissemination of a wound infection. A debridement can be effected both surgically, e.g. with scalpel and ring curette, and also enzymatically, autolytically or biosurgically. However, such treatment is mostly associated with severe pain for the patients, especially in the case of surgical debridement.

Particularly intensive and careful therapeutic measures are necessary when an acute wound turns into a chronic wound. A wound is considered chronic when its healing is not completed within a period of four to eight weeks after occurrence. Chronic wounds mostly do not occur by chance, but instead often arise in connection with clinical pictures which are associated with a weakened immune system or defective circulation. The diseases associated with poor circulation mainly of the legs include in particular type 2 diabetes mellitus, chronic venous insufficiency or peripheral occlusive arterial disease, which is also known as the so-called "claudication". In case of the aforesaid diseases, an extensive, poorly healing and infected or necrotizing chronic wound can develop even from very small wounds. In particular with infection of such wounds with microorganisms, for example the aforesaid hospital germs, complete necrosis of skin, subcutis and muscle fascia can occur, which in the worst case renders amputation of the limbs affected necessary. Particularly commonly in connection with circulatory disorders, the diabetic foot syndrome occurs, a necrotizing fasciitis or Ulcus cruris. Immunodeficiency, for example in HIV infected patients, can favor the occurrence of chronic wounds, since firstly the infection risk as such is elevated and secondly the regeneration of tissue for closure of the wounds only takes place slowly. The pressure ulcers also described as bedsores, such as mostly occur in bedridden patients because of incorrect positioning, are also termed chronic wounds, since the time for their healing also extends beyond a period of four weeks and requires particularly careful and prolonged therapeutic measures.

Wound care or wound treatment generally pursues the aim of preventing a wound infection and ensuring rapid and effective wound healing. Here how intensively and by what measures the wound healing must be supported depends on the severity, in particular the depth and area, of the wound.

Already in 1979, the American doctor T D Turner drafted various, generally recognized quality criteria for the ideal wound dressing, which even today still retain their validity.

However, the approaches for wound care or for accelerating wound healing known from the state of the art are often inadequate, since they are in many cases not satisfactory as regards the generally recognized quality criteria for wound dressings or do not enable adequate therapeutic success.

In EP 2 322 232 A2, a multilayer wound dressing is described which is based on a polysaccharide-containing gel and a layer based on another biocompatible material. However, such gel-based wound dressings are sometimes also associated with the disadvantage that owing to the already high moisture content of the gel itself, only diminished uptake of excess secretions can occur. In addition, the air permeability and the contamination protection of such wound dressings are often not satisfactory.

Further, in DE 101 08 083 A1 a wound compress is described which has an activated carbon-containing layer, which is incorporated into a textile covering for stabilization, and in addition an absorbent layer and a linen-protecting layer. It is further provided that the wound compress is equipped with a film impregnated with silver ions. However, the release of silver ions into the wound region is medically questionable in that noble metals, in particular silver ions, are suspected of involvement in the onset of neurodegenerative diseases, such as for example Alzheimer's or Parkinson's. Further, through the use of a film, both uptake and removal of wound fluids through the wound dressing and the air permeability for ventilation of the wound are significantly decreased. In particular, formation of stagnant fluid and strong immune reactions or inflammatory symptoms due to accumulated toxins can occur with such wound compresses.

In addition, DE 38 75 217 T2 corresponding to EP 0 311 364 B1 relates to a wound dressing which includes an activated carbon layer wherein at least 10% of the total pore volume of the activated carbon should be formed of mesopores, and said wound dressing should be applied sterile and in a bacteria-proof covering. However, such a wound dressing does not ensure adequate air permeability. Also, the uptake of wound fluids is not sufficient to ensure an optimal wound environment. In particular, because of its porosity, the activated carbon used is unsuitable for uptake of wound fluids.

Hence, as is clear from the above remarks, in the state of the art there is a serious lack of wound dressings or wound bandages or wound compresses which are characterized by good air permeability and/or good uptake or removal of wound fluids and the toxins contained therein and degradation products from the wound healing simultaneously with good antimicrobial action.

BRIEF SUMMARY OF THE INVENTION

Hence the present invention is based on the problem of providing a wound dressing for use in wound care, in particular of the human and animal body, which at least partly avoids or at least diminishes or attenuates the aforementioned problems in the state of the art.

In particular, the present invention is based on the problem of providing a wound dressing which improves the physiological conditions of the wound healing and in particular is able efficiently to remove wound fluids and the toxins contained therein and in addition to ensure good ventilation of the wound.

To solve the aforementioned problem, according to a first aspect of the invention, the present invention proposes a wound dressing with a multilayer structure as described herein; further advantageous configurations of this aspect of the invention are similarly described.

A further subject of the present invention, according to a second aspect of the invention, is use of a wound dressing according to the invention for therapeutic wound care as described herein; further advantageous configurations of this aspect of the invention are similarly described.

It goes without saying that particular configurations and embodiments which are only described in connection with one aspect of the invention also correspondingly apply to the other aspects of the invention, without this being expressly described.

For all the relative or percentage, in particular weight-based, quantitative information stated below, it should be noted that in the context of the composition according to the invention this information should be selected or combined by those skilled in the art such that in total 100% or 100 wt. % respectively always results, if appropriate with inclusion of further components or ingredients or additives or constituents. But to those skilled in the art this goes without saying.

Incidentally, those skilled in the art can deviate from the quantitative information stated below because of the application or individual case, without departing from the scope of the present invention.

Further, for the value or parameter information stated below, it goes without saying that these values or parameters are determined by methods familiar to those skilled in the art or standardized methods or by explicitly stated methods.

That said, the present invention is described in detail below.

DETAILED DESCRIPTION OF THE INVENTION

Figure 1:
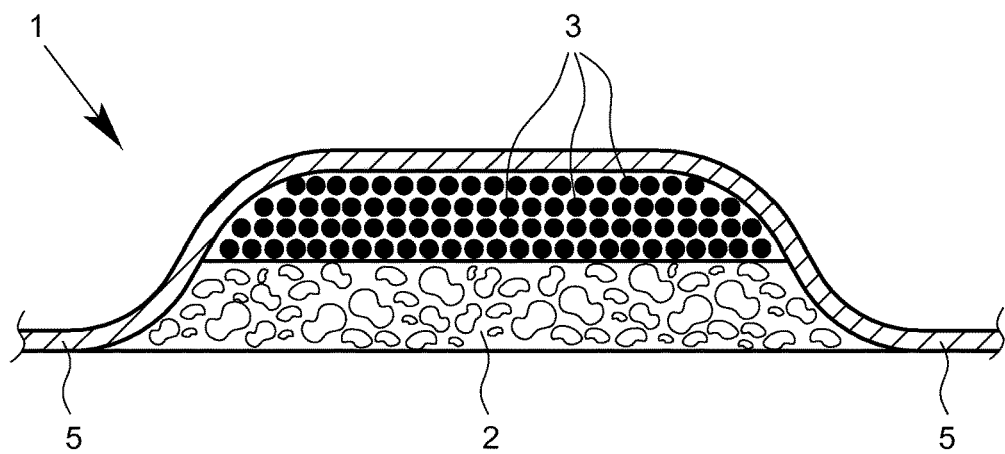
FIG. 1 provides a schematic cross-section through the layer structure of a wound dressing according to a first preferred practical example of the present invention corresponding to a specific embodiment, FIG. 2 provides a schematic cross-section through the layer structure of a wound dressing according to a further preferred practical example of the present invention corresponding to a further specific embodiment, and FIG. 3 provides a schematic cross-section through the layer structure of a wound dressing according to a further preferred practical example of the present invention corresponding to a further specific embodiment.

Thus, according to a first aspect of the invention, the subject of the present invention is a wound dressing which is suitable in particular for therapeutic wound care, wherein the wound dressing comprises at least one air permeable layer with a porous or foam-based structure, in particular in the form of a solid foam ("foam layer"), and at least one sorbent agent in the form of activated carbon.

Surprisingly, in the context of the present invention it was found by the applicant that the specific combination of an air permeable layer in the form of a porous or foam-based structure with activated carbon in the context of the production of a wound dressing leads in the use thereof to significantly improved wound healing, in particular with increased air permeability, removal or absorption of wound fluids and contamination protection, where in the context of the present invention the efficacy of the individual measures, namely provision of a foam-based structure on the one hand and activated carbon on the other in the wound dressing according to the invention, surpasses the effect of the individual measures, which can be seen as an indication of the presence of a synergistic effect.

As regards the term "wound dressing", as used in the context of the present invention, this in general in particular describes dressings for topical application onto external wounds, in order to prevent penetration of foreign bodies into the wound and to absorb blood and wound secretions. According to the invention, terms such as "wound plaster", "wound bandage" or "wound covering" can also be used synonymously.

The air permeable layer is in particular a wound-covering layer, where this term should further be understood to mean that this is a layer facing the wound to be treated in the worn and/or use state. In particular, in the application or use state of the wound dressing according to the invention, the wound-covering layer at least essentially completely lies on the wound to be treated or is at least essentially completely in contact with the wound to be treated. It is thus an essential component of the wound dressing for the primary uptake of wound fluids on the one hand and for protection of the wound from mechanical influence on the other.

In the context of the present invention, the term "air permeable layer with porous or foam-based structure" or "foam layer" should be understood to mean a foam solid at room temperature (20° C.) and atmospheric pressure (1.013 bar) (i.e. not a liquid or viscous foam). In this connection, it should in particular be emphasized that "solid" does not mean a rigid state. In other words, according to the invention it is preferable that the foam nonetheless has a flexible or elastic structure and so-to-speak is reversibly deformable and/or compressible. Generally defined as solid foams are structures of gas-filled, in particular air-filled, spherical or polyhedral pores or cells which are bounded by solid cell struts and/or lamellae. The cell struts and/or lamellae based on a material constituting the foam, which are so-to-speak linked by nodal points, thereby form a connected framework. In other words, overall a porous structure is formed by the gas-filled or air-filled cells within the cell struts and/or lamellae. If the cell struts or lamellae are only incompletely formed or partially destroyed, an open-cell and/or open-pore foam, which is preferable according to the invention, is formed. To form the foam, in general a gas, preferably air, is blown into a liquid which contains the foam-forming material or consists thereof. Foam formation by vigorous shaking, beating, spraying or stirring of the liquid or suspension in the relevant gas atmosphere is also possible. Further, foam formation can be effected by chemical reactions which are associated with the formation of gases. Next or simultaneously, curing to give the resulting foam takes place. For further details on the term "foam", reference can be made to Römpp, Chemical Lexicon, $10^{th}$ Edition, Georg Thieme Verlag, Stuttgart/New York, keyword "foam", pages 3950 and 3951 and the literature cited therein, the whole content whereof relating to this is by reference completely included herein.

As regards the use of a solid foam in the wound dressing, the pore system or porous structure serves in particular for the uptake of wound exudate in the air-filled pores. The wound fluids taken up are retained in the pores by capillary and/or adhesive forces and do not get back into the wound. In addition, through its mechanical properties, such as the compressibility or deformability, such a pore system affords a damping or buffering action for protection against external mechanical influences. Further, outstanding ventilation of the wound is ensured by the open-pore foam in particular.

As regards the activated carbon contained in the wound dressing according to the invention, this is in particular a bacteriostatic or antimicrobial component which inhibits the growth of bacteria and thus efficiently prevents the spread of bacteria in the wound to be treated. In particular, according to the invention an activated carbon with special biostatic or biocidal, in particular antimicrobial action, which efficiently prohibits the growth of microorganisms, in particular of bacteria, in the wound is used. In particular, the activated carbon used according to the invention, in particular with a high micropore content, causes the microorganisms to be permanently bound or immobilized (which finally leads to their death, since the immobilization on the activated carbon both of the microorganisms themselves and also the possible nutrients prevent an adequate nutrient supply).

In addition, activated carbon can also take up or bind large quantities of wound fluids, so that formation of stagnant fluid in the wound is prevented. Further, the activated carbon enables the adsorption of unpleasant-smelling substances, such as in particular arise with extensive and necrotizing tissue breaks.

Topical and sometimes wound healing-inhibiting or even toxic degradation products, such as arise firstly through the metabolic products associated with wound healing and secondly as a result of wound infections, are also taken up and rendered harmless by the activated carbon. Furthermore, the activated carbon can also serve as a moisture buffer: excess water or excess moisture can be temporarily stored or buffered and as necessary released again, so that an ideal environment for the wound healing process is ensured, whereby with very good ventilation, drying out of the wound on the one hand, but also an excessively moist environment on the other, are counteracted; in this manner, an ideal moisture environment for the healing process is provided. Moreover, activated carbon is not associated with any kind of side-effects and in particular is toxicologically completely harmless.

The combination of a foam layer with activated carbon leads to a synergistic effect as regards wound healing, since the two components, foam layer on the one hand and activated carbon on the other, complement and in addition strengthen one another's mode of action.

Without wishing to be limited to this theory, the air permeable layer by means of its porous or foam-based structure makes it possible, with good ventilation of the wound, for wound fluids to be taken up or removed from the wound region in large quantities, so that firstly the formation of stagnant fluid and secondly the accumulation of toxins and topical degradation products is prevented. This effect is still further reinforced by the activated carbon used according to the invention, since this can both absorb wound fluids and also immobilize, and sometimes even degrade, toxins and topical degradation products. In addition, and this also without wishing to be limited to this theory, the particularly high air permeability of the air permeable layer or the foam layer, which is at least essentially not impaired by the activated carbon, enable the wound to be treated, in spite of being extensively covered, nonetheless to be simultaneously excellently aerated and protected against mechanical influences. Also, through the additional biostatic or biocidal, in particular antimicrobial or bacteriostatic, action of the activated carbon, outstanding contamination protection is ensured, so that not only can the physiological conditions for acceleration of the wound healing be improved, but also pathogens can be efficiently removed and the infection risk falls still further. Thus as a result, with the wound dressing according to the invention a wholly improved concept is implemented, which effects an improvement or acceleration of wound healing at several levels, as could not previously be achieved with the state of the art wound dressings.

Overall, the wound dressing according to the invention is associated with many further advantages, improvements and special features which characterize the present invention compared to the state of the art and which can be non-limitingly summarized as follows:

With the present invention, for the first time a wound dressing is provided which significantly accelerates wound healing, in particular that of complex or complicated to treat or chronic wounds, but in addition however is particularly well tolerated and affords excellent contamination protection.

Overall, the use of the wound dressing according to the invention leads to accelerated cessation of exudation and to rapid onset of the granulation phase, due in particular to the outstanding ventilation of the wound and the removal of wound fluids, so that rapid wound closure can take place. As regards the improved wound healing, reference can already be made at this point to the use and efficacy studies conducted by the applicant and stated below, which confirm the outstanding efficacy, which is described in still more detail later.

Overall, both the air permeable layer and the foam layer as such and the whole resulting wound dressing have particularly high air permeability, such as could not hitherto be attained in the state of the art.

In particular, the wound dressing according to the invention offers the advantage that because of the supplementary use of activated carbon as well as the foam-based structure, it can absorb the exudate or wound fluids such as in particular emerge from extensive wounds, in still greater quantities. Thus it is ensured that while the moist environment necessary for good wound healing is maintained in the wound, the formation of stagnant fluid, which in turn would retard wound healing and increase the infection risk, is however prevented and moreover toxic degradation products are removed. This results not only in the mere uptake of exudate and degradation products by the air permeable layer and the activated carbon, but rather the degradation products are also rendered harmless by means of the activated carbon through immobilization and degradation.

Further, the wound dressing according to the invention is able to maintain a moist-warm environment during the treatment of the wound, in order to enable the provision of the tissue with nutrients and to prevent drying out (indeed if the wound dries out, the tissue defect is still further enlarged by the dying of cells; further, drying slows the healing process, since as a result of the deficient provision the function of the defensive cells is impaired and the enzymatic activity in the regeneration of tissue is disturbed). With the wound dressing according to the invention, the temperature is also held at an optimal temperature for the physiological processes of wound healing.

In addition, the wound dressing according to the invention offers excellent protection against infection by typical hospital germs such as *Staphylococcus aureus, Staphylococcus epidermidis, Proteus mirabilis, Escherichia coli* and *Pseudomonas aeruginosa*, as is also clear from the inhibition zone test performed in the context of the practical examples according to the invention. Thus the wound dressing according to the invention is an excellent basis for the therapy of wounds infected with multiresistant strains without the use of antibiotics. This is especially advantageous as regards patients with an already weakened immune system since the administration of many antibiotics stresses the immune system still further. In addition, decreased use of antibiotics for therapeutic purposes generally contributes to the containment of the appearance and dissemination of multiresistant germs.

Further, as well as the aforesaid properties, because of the strongly adsorbent activated carbon, during use of the wound dressing according to the invention unpleasant odors such as occur in particular with extensive or necrotizing wounds are adsorbed, which is of particular importance for the patient's wellbeing, since those affected often suffer more strongly from the unpleasant phenomena associated with such a wound, such as a strong odor, than from the wound as such.

Further, the wound dressing according to the invention is characterized by its extremely good tolerability simultaneously with good contamination protection. In contrast to wound dressings according to the invention, with state of the art wound dressings satisfactory contamination protection is often only achieved by the use of noble metals, in particular silver. However, the topical use of such metals is extremely questionable in terms of health, since silver in particular can enter cells and is suspected of being involved in triggering diseases such as Alzheimer's or Parkinson's.

In addition, the wound dressing according to the invention displays good adhesion relative to the wound without however in the process adhering to the wound bed. Also, the wound dressing according to the invention is designed such that no fibers or other foreign matter can be released onto the wound (which otherwise could again lead to inflammatory reactions). In this connection, the air permeable layer or the foam material layer in particular also has the effect that the wound dressing as a whole is particularly flexible and is in optimal contact with the wound, in particular over the whole area, without the formation of cavities or intervening spaces.

Hence, as a result an efficient wound dressing is provided according to the invention, whose exceptional efficacy is based in particular on the specific, in particular synergistic, combination of a foam layer on the one hand and activated carbon on the other.

The wound dressing according to the invention can be configured in many ways. For better understanding, possible forms and configurations are illustrated below:

According to the invention, it is particularly preferable if the air permeable layer is made flexible and/or deformable, in particular elastically and/or reversibly deformable, and/or compressible, in particular elastically and/or reversibly compressible. Through such a configuration, the wound dressing according to the invention adapts itself optimally to the wound to be treated, i.e. it lies optimally on the wound. In particular, it is thus possible for the wound to be in contact with the wound dressing completely and so-to-speak no "air space" or "cavity" to form between wound and wound dressing, which is especially important as regards the uptake of wound fluids.

As further regards the air permeable layer, this is preferably formed by a foam present in the solid aggregation state at room temperature (20° C.) and atmospheric pressure (1.01325 bar), in particular a naturally based, nature-identical or synthetic foam.

Further, it is particularly preferable according to the invention if the air permeable layer has an essentially open pore structure and is made with open pores and/or open cells. In particular, the air permeable layer can be made as an open-cell foam. Through such an open-cell or open-pore foam, in particular the air permeability and the uptake or removal of wound exudate is improved, since such a foam is especially accessible and has optimal uptake and flow properties.

In addition, it is particularly preferable according to the invention if the permeable layer has a compressive hardness in the range from 1 to 100 kPa, in particular 2 to 75 kPa, preferably 5 to 50 kPa. Compressive hardness is understood to mean the pressure in pascals (Pa) physically acting on an area in square meters ($m^2$) which as per DIN 53577 is necessary to compress the foam by 40%, based on the starting pressures. The compressive hardness is generally determined or measured as per DIN EN ISO 3386-1. As regards the compressive hardness with reference to the wound dressing according to the invention, this is of high relevance particularly in connection with protection from mechanical influence on the wound and the shape flexibility or adaptability to the wound bed. In other words, through the compressive hardness specified according to the invention, optimal laying onto or complete contact with the wound bed is enabled, but adequate protection against mechanical influences is nonetheless allowed.

In connection with the good adaptation of the wound dressing to the wound bed simultaneously with good protection against mechanical wounds, it can further be provided according to the invention that the air permeable layer has a compressive modulus in the range from 1 to 750 MPa, in particular 5 to 500 MPa, preferably 10 to 250 MPa, especially preferably 25 to 100 MPa. The compressive modulus is an intrinsic or substance-specific quantity from elasticity theory and describes the all-round pressure change necessary to cause a defined volume change (without phase transition). The compressive modulus is determined or measured as per DIN EN 100 844.

In addition, it can be provided according to the invention that at room temperature (20° C.) and atmospheric pressure (1.01325 bar) the air permeable layer has a specific gravity (bulk density) in the range from 5 to 200 kg/m$^3$, in particular 7.5 to 100 kg/m$^3$, preferably 10 to 30 kg/m$^3$. The specific gravity is calculated from the ratio of the mass of the air permeable layer to its volume and in the case of pore-containing or porous bodies takes account of the enclosed air.

As regards the air permeability of the foam layer, this is usually particularly high according to the invention in order to enable good ventilation of the wound. In this connection, it is preferable according to the invention if the air permeable layer has an air permeability of at least 10 $l \cdot m^{-2} \cdot sec^{-1}$, in particular at least 30 $l \cdot m^{-2} \cdot sec^{-1}$, preferably at least 50 $l \cdot m^{-2} \cdot sec^{-1}$, especially preferably at least 100 $l \cdot m^{-2} \cdot sec^{-1}$, quite particularly preferably at least 500 $l \cdot m^{-2} \cdot sec^{-1}$, and/or up to 10,000 $l \cdot m^{-2} \cdot sec^{-1}$, and in particular up to 20,000 $l \cdot m^{-2} \cdot sec$ at a flow resistance of 127 Pa.

As regards the air permeability of the whole wound dressing (i.e. not only the air permeable layer), this is somewhat lower than that of the air permeable layer, but nonetheless sufficiently high to ensure outstanding ventilation of the wound. In this connection, it can be provided according to the invention that the wound dressing as a whole is made air permeable, in particular with an air permeability of at least 5 $l \cdot m^{-2} \cdot sec^{-1}$, in particular at least 25 $l \cdot m^{-2} \cdot sec^{-1}$, preferably at least 40 $l \cdot m^{-2} \cdot sec^{-1}$, especially preferably at least 100 $l \cdot m^{-2} \cdot sec^{-1}$, quite particularly preferably at least 250 $l \cdot m^{-2} \cdot sec^{-1}$, and/or up to 5,000 $l \cdot m^{-2} \cdot sec^{-1}$, and in particular up to 10,000 $l \cdot m^{-2} \cdot sec^{-1}$ at a flow resistance of 127 Pa.

The aforesaid statements on air permeability describe the permeability to air in the direction normal to the surface, i.e. perpendicular to the plane or perpendicular to the main plane of the wound dressing.

As regards the structure of the wound dressing according to the invention, this can be extremely diverse and in particular purpose-specific:

According to a particularly preferred embodiment of the present invention, it can be provided that the wound dressing has the activated carbon in the form of at least one layer containing the activated carbon ("activated carbon layer"). Further, it can be provided that the wound dressing has a multilayer structure.

According to a particularly preferred embodiment of the present invention, it can be provided that the wound dressing has a multilayer structure, wherein the multilayer structure comprises at least one air permeable layer with a porous and/or foam-based structure, in particular in the form of a solid foam ("foam layer"), and at least one layer containing activated carbon ("activated carbon layer").

As regards the materials used for the air permeable layer, various configurations are also possible:

According to a first preferred embodiment, it can be provided that the air permeable layer comprises at least one layer containing hydrocolloid, preferably collagen, ("hydrocolloid layer" or "collagen layer") or is formed thereof.

As regards the term "hydrocolloid", as used in the context of the present invention, this is to be understood very broadly. In general, hydrocolloids are understood to be at least partly water-soluble, natural, but also synthetic, polymers which form gels or viscous solutions or suspensions in aqueous systems. They are usually substances which belong to the protein or polysaccharide classes, with a large number of hydrocolloids originating from nature, in particular from land plants, algae, animals and bacteria. Hydrocolloids are often used as thickeners in cosmetics and products of the food industry. For further details on the term hydrocolloid, reference can in particular be made to Römpp, Chemical Lexicon, $10^{th}$ Edition, Georg Thieme Verlag, Stuttgart/New York, keyword "hydrocolloids", page 1837, including the literature cited therein, the content whereof relating to this is by reference completely included herein.

The hydrocolloid of the air permeable layer present according to the invention can in particular be a material of porcine, bovine and/or equine origin, preferably of porcine origin, in particular from porcine skin. A collagen material with the aforesaid properties is commercially available, in particular via Medichema® GmbH, Chemnitz, German Federal Republic.

In this connection, it is particularly preferable according to the invention if the hydrocolloid of the air permeable layer is selected from the group of polysaccharides and proteins, in particular plant, animal or bacterial polysaccharides and proteins. In particular, the hydrocolloid can be selected from the group of collagen, cellulose and cellulose derivatives, glycosaminoglycans (in particular acidic glycosaminoglycans, preferably hyaluronic acid and/or salts thereof), pectins, gum arabic, galactomannans, agar, carrageen, alginates, gelatin, caseinates, xanthans, dextrans and scleroglucans. Quite especially preferably, the hydrocolloid is collagen, hyaluronic acid and/or salts thereof and/or gelatin, in particular collagen.

Collagen consists of long-fiber, linear colloidal and high molecular weight scleroproteins of the extra-cellular matrix, which occur in the connective tissue, in particular in the skin, in cartilage and in tendons, ligaments and blood vessels and the protein-containing ground substance of the bones of vertebrates, but also in phylogenetically early life-forms such as sponges or sea anemones. The fibrous structure of collagen is due in particular to the occurrence of glycine at every third position in the amino acid sequence, since as a very compact amino acid glycine results in a specific, helical secondary structure of proteins. On the other hand, the amino acids tryptophan and tyrosine also known as so-called helix breakers and the disulfide bridge-forming amino acid cysteine are generally not present in collagens. For further details on the term collagen, reference can also be made to Römpp, Chemical Lexicon, $10^{th}$ Edition, Georg Thieme Verlag, Stuttgart/New York, keyword "hydrocolloids", pages 796 and 797, and the literature cited therein, the content whereof relating to this is by reference completely included herein.

Specifically as regards the use of collagen in the context of the wound dressing according to the invention, this is capable of significantly improving the wound healing process. In particular, collagen has a protease-inhibiting action which serves to lower the elevated protease level in the wound area detrimental to the wound healing. To be precise, if the protease level in the wound area is elevated, this often leads to uncoordinated wound healing and to the destruction of growth factors since these are degraded by proteases, such as for example neutrophilic elastases or matrix-metalloproteases (MMPs). Further, collagen stimulates the formation of vascular structures and connective tissue and thus supports the restoration of the structural stability of the tissue. In this sense, the wound healing can be extremely efficiently supported by use of collagen as the hydrocolloid.

Similar remarks also apply to gelatin, which can also be preferably used as the hydrocolloid in the wound dressing: the term "gelatin" is usually and in the context of the present invention understood to mean a polypeptide which is mainly obtained by hydrolysis of the collagen contained in the skin and bones of animals under acidic or basic conditions. Here the obtention of gelatin under acidic conditions results in the so-called type A gelatin and under basic conditions in the so-called type B gelatin. In water, in particular under the simultaneous action of heat, gelatin firstly swells markedly and dissolves therein with formation of a viscous solution, which finally sets like a jelly below 35° C. For further details on the term gelatin, reference can be made to Römpp, Chemical Lexicon, $10^{th}$ Edition, Georg Thieme Verlag, Stuttgart/New York, keyword "gelatin", page 1484, and the literature cited therein, the content whereof relating to this is by reference completely included herein.

As further regards the air permeable layer, it can be provided according to the invention that this is based on a hydrocolloid nonwoven and/or hydrocolloid foam, preferably a collagen nonwoven and/or collagen foam. In this connection, it can in particular be provided that the air permeable layer is based on hydrocolloid non-woven and/or hydrocolloid foam, preferably collagen nonwoven and/or collagen foam of porcine, bovine and/or equine origin, and particularly preferably based on hydrocolloid non-woven and/or hydrocolloid foam, preferably collagen nonwoven and/or collagen foam of porcine origin.

In a manner particularly preferred according to the invention, it can be provided that the air permeable layer is formed of a hydrocolloid nonwoven and/or hydrocolloid foam, preferably collagen nonwoven and/or a collagen foam, in particular of a hydrocolloid nonwoven and/or hydrocolloid foam, preferably collagen nonwoven and/or a collagen foam, of porcine, bovine and/or equine origin, and preferably of a hydrocolloid nonwoven and/or hydrocolloid foam, preferably collagen nonwoven and/or a collagen foam of porcine origin.

The use of hydrocolloid nonwoven and/or hydrocolloid foam, preferably collagen nonwoven and/or collagen foam is associated with the advantage, compared to conventional materials for the production of wound dressings, that the material does not adhere to the wound bed, but nonetheless good adhesion to the surface can be achieved. Furthermore, it is particularly advantageous that wound dressings based on hydrocolloid foam or hydrocolloid nonwoven, in particular collagen foam or collagen nonwoven, release no fibers or particles into the wound and thus the penetration or additional introduction of foreign bodies is prevented.

In this connection, it has been found particularly advantageous if the wound dressing contains hydrocolloid foam, in particular collagen foam, i.e. hydrocolloid or collagen solidified and expanded into a foam, since in addition large volumes of wound fluids can efficiently flow out of the wound area through pores contained in the hydrocolloid foam or collagen foam, so that the formation of stagnant fluid and excessively long contact of substances contained in the wound fluids and detrimental to wound healing with the wound itself is prevented. At the same time, however, the chemical and physical properties of solidified and expanded hydrocolloid or collagen (i.e. hydrocolloid or collagen foam)

prevent the wound from drying out. In addition, such foams are extremely well adaptable to the shape of the wound bed, i.e. they can cover the wound completely or extensively, without bulges or the like occurring. Furthermore, with the use of a hydro-colloid foam or a collagen foam, particularly good gas permeability is enabled. This is associated in particular with the advantage that the wound is well ventilated, in particular with oxygen, which on the one hand favors the physiological wound healing processes and on the other also prevents the growth of germs which live anaerobically, for example of the genus *Clostridium*.

Hence as a result through the provision of the colloid layer or collagen layer, on the one hand wound fluids are efficiently removed and on the other gas permeability is ensured.

As further regards the air permeable layer, it can be provided according to the invention that this is obtainable by application of a dispersion or solution of a hydrocolloid, preferably of a collagen, onto a support followed by drying, in particular lyophilization (freeze-drying), preferably with expansion of the hydrocolloid, in particular the collagen. A hydro-colloid, preferably collagen, suspension or solution suitable according to the invention is obtainable in particular by suspending or solubilizing the hydrocolloid, in particular collagen, in water, in particular high purity water or in disinfected, sterile or sterilized water. Here the hydrocolloid, preferably collagen, can preferably be contained in the suspension or solution in a quantity in the range from 0.1 to 5 wt. %, in particular 0.5 to 4 wt. %, preferably 0.7 to 3 wt. %, and especially preferably 1 to 2 wt. %, based on the hydrocolloid suspension or solution, preferably collagen suspension or solution. Finally, the dried and expanded hydrocolloid, preferably collagen, can be removed from the support and then used for production of the wound dressing. To ensure the desired properties, the hydrocolloid or the relevant layer with the hydrocolloid can have a defined residual moisture content, which is known to those skilled in the art.

According to an alternative embodiment of the present invention, it can equally be provided that the air permeable layer includes at least one synthetically produced open-cell foam based on at least one organic polymer or is formed thereof. Here it is preferred if the organic polymer is selected from the group of polyurethanes, polyolefins, polystyrenes, polyvinyl chlorides, polyisocyanurates and formaldehyde resins. However, polyurethanes are particularly preferred. The aforesaid polymers are characterized in particular by their outstanding tolerability on the skin and in addition are particularly easy to handle in processing. In particular, the aforesaid materials form foams with a particularly homogeneous pore system, which further increases the water and moisture uptake (improved absorbent efficacy) and air permeability.

Furthermore, it is preferred according to the invention if the air permeable layer is or forms an outer layer of the wound dressing. In this connection, it can in particular be provided that in the application or use state of the wound dressing the air permeable layer is arranged on the side of the wound dressing facing the wound to be treated.

As regards the dimensions of the air permeable layer, this preferably has a thickness in the range from 0.01 to 100 mm, in particular 0.02 to 50 mm, preferably 0.05 to 10 mm. Depending on the severity of the wound to be treated and the degree of wound exudation, it is advantageous, particularly in case of heavy secretion of wound fluids (particularly for example in the exudative phase of wound healing), if the foam layer is made especially thick. On the other hand, with wounds already advanced in the healing process it is mostly sufficient to use markedly thinner air permeable layers. Hence according to the invention it is possible to adapt the thickness of the foam layer to the particular requirements.

In this connection, it can be provided according to the invention that the air permeable layer makes up 5% to 95%, in particular 10% to 80%, preferably 20% to 60%, of the total thickness of the wound dressing.

As is further explained below the activated carbon contained in the wound dressing can also be adapted by very specific selection to the demands placed on the particular wound dressing according to the invention.

As regards the physical form or three-dimensional configuration of the activated carbon contained in the wound dressing, this is preferably a granular, in particular spherical, activated carbon and/or activated carbon fibers, in particular in the form of an activated carbon fiber fabric, preferably however a granular, in particular spherical, activated carbon. As regards the bacteriostatic or antimicrobial action and the uptake of wound fluids, the use of spherical activated carbon has proved especially efficient. A granular, in particular spherical, activated carbon offers the advantage of especially good processability, particularly with regard to attachment to a planar, preferably textile support and good mechanical strength so that no dust and no impurities are released.

According to a preferred embodiment of the present invention, it is provided that the activated carbon is made as a granular, in particular spherical, activated carbon with absolute particle sizes in the range from 0.01 to 3 mm, in particular in the range from 0.02 to 2 mm, preferably in the range from 0.05 to 1.5 mm, particularly preferably in the range from 0.1 to 0.8 mm and quite especially preferably in the range from 0.2 to 0.6 mm. Equally, it can be provided that the activated carbon is a granular, in particular spherical, activated carbon with average particle sizes, in particular determined as per ASTM D2862-97/04, in the range from 0.05 to 2.5 mm, in particular in the range from 0.1 to 2 mm, preferably in the range from 0.15 to 1 mm and quite especially preferably in the range from 0.2 to 0.6 mm.

The following parameter information for the activated carbon used according to the invention is determined or ascertained by standardized or explicitly stated determination methods or determination methods familiar per se to those skilled in the art. Unless otherwise stated below, this parameter information is obtained in particular from the nitrogen adsorption isotherms of the activated carbon.

As regards the nature of the activated carbon used, it has further proved particularly advantageous if the activated carbon has a micropore volume content formed of micropores with pore diameters of ≤20 Å, based on the total pore volume of the activated carbon, of at least 60%, in particular at least 65%, preferably at least 70%, based on the total pore volume of the activated carbon. In particular, it is advantageous if the activated carbon has a micropore volume content formed of micropores with pore diameters of ≤20 Å, based on the total pore volume of the activated carbon, in the range from 60% to 95%, in particular in the range from 65% to 90%, and preferably in the range from 70% to 85%. As regards the remaining pore volume content of the activated carbon used, this is formed of meso- and macropores.

In the context of the present invention, the term micropores describes pores with pore diameters up to 20 Å inclusive, whereas the term mesopores describes pores with pore diameters from >20 Å to 50 Å inclusive, and the term macropores describes pores with pore diameters >50 Å.

Through the high micropore content, better sorption of wound fluids and odorous substances can in particular be achieved. In addition, the bacteriostatic or antimicrobial action is significantly improved compared to activated carbon of high meso- and macropore content. Further, an activated carbon of high micropore content has the advantage that microorganisms can be permanently bound or immobilized.

Furthermore, it can be provided according to the invention that the activated carbon has a micropore volume content formed of micropores with pore diameters of ≤20 Å, in particular a micropore volume by the carbon black method, of at least 0.40 cm$^3$/g, in particular at least 0.45 cm$^3$/g, preferably at least 0.50 cm$^3$/g. In particular, it can be provided according to the invention that the activated carbon has a micropore volume content formed of micropores with pore diameters of ≤20 Å in particular a micropore volume by the carbon black method, in the range from 0.40 cm$^3$/g to 2 cm$^3$/g, in particular in the range from 0.45 cm$^3$/g to 1.5 cm$^3$/g, preferably in the range from 0.50 cm$^3$/g to 1.2 cm$^3$/g.

The determination method by the carbon black method is known per se to those skilled in the art, so that no more details are needed concerning this. Further, for more details on the determination of the pore area and the pore volume by the carbon black method, reference can for example be made to R. W. Magee, Evaluation of the External Surface Area of Carbon Black by Nitrogen Adsorption, Presented at the Meeting of the Rubber Division of the American Chem. Soc., October 1994, e.g. cited in: Quantachrome Instruments, AUTOSORB-1, AS1 WinVersion 1.50, Operating Manual, OM, 05061, Quantachrome Instruments 2004, Florida, USA, pages 71ff.

As regards the micropore surface area content of the activated carbon used according to the invention, in the context of the present invention it can be provided that the activated carbon has a specific micropore surface area content, in particular a specific micropore surface area content formed of pores with pore diameters of ≤20 Å, of at least 50%, in particular at least 60%, preferably at least 70%, and quite especially preferably at least 75%, based on the specific total surface area (BET) of the activated carbon.

Furthermore, it is preferred according to the invention if the activated carbon has an internal surface area (BET) in the range from 500 to 3,000 m$^2$/g, in particular in the range from 800 to 2,000 m$^2$/g, preferably in the range from 900 to 1,800 m$^2$/g, and especially preferably in the range from 1,000 to 1,600 m$^2$/g.

The determination of the specific surface area according to BET is essentially known per se to those skilled in the art, so that no more details are needed concerning this. All BET surface area information is based on the determination as per ASTM D6556-04. In the context of the present invention, the so-called multipoint BET determination method (MP-BET) in a partial pressure range p/p0 from 0.05 to 1 is used for the determination of the BET surface area. With regard to further details on the determination of the BET surface area or on the BET method, reference can be made to the aforesaid ASTM D6556-04 and to Römpp, Chemical Lexicon, 10$^{th}$ Edition, Georg Thieme Verlag, Stuttgart/New York, keyword "BET method", including the literature cited therein, and to Winnacker-Küchler (3$^{rd}$ Edition, Volume 7, pages 93ff and to Z. Anal. Chem. 238, pages 187 to 193 (1968).

In order to achieve good overall efficacy of adsorption performance, in particular as regards the adsorption of wound fluids and odorous substances, and the bacteriostatic or antimicrobial action, it is also advantageous according to the invention if the activated carbon has a total pore volume, in particular a total pore volume as per Gurvich, in the range from 0.1 to 4 cm$^3$/g, in particular in the range from 0.2 to 3 cm$^3$/g, preferably in the range from 0.3 to 2.5 cm$^3$/g and especially preferably in the range from 0.5 to 2 cm$^3$/g.

As regards the determination of the total pore volume as per Gurvich, this is a measurement or determination method known per se to those skilled in the art in this field. For further details concerning the determination of the total pore volume as per Gurvich, reference can for example be made to L. Gurvich (1915), J. Phys. Chem. Soc. Russ. 47, 805 and to S. Lowell et al., Characterization of Porous Solids and Powders: Surface Area Pore Size and Density, Kluwer Academic Publishers, Article Technology Series, pages 111ff.

In order to prevent some of the activated carbon itself from penetrating as foreign bodies into the wound, it is particularly advantageous if the activated carbon is configured such that at least essentially no particles or dust are released into the surroundings. In this connection, according to the invention it is preferred if the activated carbon has a pressure or burst strength, in particular a weight loading capacity per activated carbon particle, in particular per activated carbon grain or activated carbon sphere, of at least 10 Newtons, in particular at least 15 Newtons, preferably at least 20 Newtons. Equally, it can be provided according to the invention if the activated carbon has a pressure or burst strength, in particular a weight loading capacity per activated carbon particle, in particular per activated carbon grain or activated carbon sphere, in the range from 10 to 50 Newtons, in particular in the range from 12 to 45 Newtons, preferably in the range from 15 to 40 Newtons.

In the context of the present invention, it is preferred if the activated carbon is made at least essentially abrasion-resistant and/or at least essentially dustless. The outstanding abrasion resistance and the dustlessness of the activated carbon used make it possible for the wound to be treated not to be contaminated by materials or impurities (such as for example activated carbon dust) of the wound dressing.

As stated above, the abrasion hardness of the activated carbon used according to the invention should be made extremely high: thus the abrasion resistance of the activated carbon used according to the invention by the method according to CEFIC (Conseil Européen des Fédérations de l'Industrie Chimique, Avenue Louise 250, Bte 71, B-1050, Brussels, November 1986, European Council of Chemical Manufacturers' Federations, Test methods for activated carbons, Article 1.6 "Mechanical Hardness", pages 18/19) is advantageously 100%. Also as per ASTM D3802, the abrasion resistance values of the activated carbon used according to the invention should be 100%.

In particular, it can be provided according to the invention that the activated carbon has a fractal dimension of the open porosity of at least 2.3, in particular of at least 2.4, preferably of at least 2.5 and especially preferably of at least 2.7. The fractal dimension of the open porosity can be determined in particular as per WO 2004/046033 A1 or DE 102 54 241 A1 and characterizes in particular the roughness, in particular microroughness, of the inner surface of the activated carbon. This value should thus be seen as a measure of the microstructuring of the inner surface of the activated carbon. The greater is the value for the parameter of the fractal dimension of the open porosity and thus the surface roughness of the activated carbon, the more strongly marked is the ability of the activated carbon to create more irregularities of the electronic state density functions at the inner surface of the activated carbon capable of bonding or at least having an attracting action, associated with the result of increased or improved binding of species to be sorbed, in particular adsorbed. The improvement of the binding comprises firstly an increase in the packing density within an adsorbed monolayer (and hence an increase in the adsorption capacity) and secondly an increased binding strength. On the basis of the selection of an activated carbon with such values for the fractal dimension of the open porosity, in the context of the wound dressing according to the invention, species such as in particular microorganisms, toxins, etc. can be sorptively or adsorptively bound to an increased extent, in particular with better loading or capacity and with greater irreversibility.

To further improve the overall mode of action of the wound dressing according to the invention, particularly as regards contamination protection and promotion of wound healing, it has proved quite especially advantageous further to increase the biocidal and/or biostatic, in particular antimicrobial properties of the activated carbon used in a specific manner. As regards the term "biocidal properties", this should be understood to mean that microorganisms in particular are killed and/or degraded through the biocidal properties. In the context of the present invention, microorganisms are understood to comprise both bacteria and also fungi, but in addition also viruses. Thus biocidal properties in the sense of the present invention are understood equally to be bactericidal, fungicidal and/or virucidal properties. In contrast, the growth or proliferation of microorganisms, in particular bacteria, fungi and viruses, are mainly inhibited by "biostatic properties". Thus biostatic properties in the sense of the present invention are understood equally to be bacteriostatic, fungistatic and/or virostatic properties. As regards the activated carbon as such to be used for this purpose, it is advantageous to use synthetic or synthetically produced activated carbon.

As further regards the biocidal and/or biostatic, in particular antimicrobial action and/or treatment of the activated carbon, it can be provided according to the invention that this is achieved through the activated carbon production process, in particular production by pyrolysis and subsequent activation of organic polymers. The action and/or treatment of the activated carbon described above results in particular from the surface charge and/or hydrophobicity and/or textural properties generated in the context of the production process. As regards the starting polymers for the production of the activated carbon, these can in particular be polystyrenes, preferably divinylbenzene-crosslinked polystyrenes.

In this connection, it should in particular be emphasized that the outstanding antimicrobial efficacy of the activated carbon used according to the invention is based on the fact that the properties described above, in particular in combination with a high micropore volume, respond in particular to polarities of (bio)molecules and (bio)particles. As regards the adsorption of microorganisms, in particular bacteria, without wishing thereby to be limited to this theory, the activated carbon used according to the invention is made such that in particular an affinity exists to the molecules anchored in and/or on the cell wall of the microorganisms.

As regards the biocidal and/or biostatic, in particular antimicrobial action and/or treatment of the activated carbon specifically, this can also take place through an optimized additional treatment, in particular impregnation, of the activated carbon with at least one biocidal and/or biostatic, in particular antimicrobial active substance, in particular as further defined below, or be increased thereby.

Through the additional treatment, in particular impregnation, of the activated carbon with at least one biocidal and/or biostatic, in particular antimicrobial active substance, the inherent biostatic or biocidal, in particular antimicrobial properties of the activated carbon per se due in particular to the activated carbon production process are additionally reinforced by the antimicrobial properties of the active substance. The treatment, in particular impregnation, of the activated carbon is effected in a manner known per se to those skilled in the art, for example by contacting the activated carbon with the specified active substance or a solution and/or dispersion containing the active substance. Such contacting can for example be effected by spraying, slurrying, impregnation and the like.

As further regards the activated carbon used according to the invention, this is in general free from metal impregnations. Thus metal impregnations (e.g. based on silver or silver ions) are not provided in the treatment and/or impregnation of the activated carbon used according to the invention. In this manner, harmful side effects are efficiently prevented. However, in particular through the combination with the hydrocolloid layer, preferably collagen layer, good efficacy of action is ensured.

An activated carbon with the aforesaid properties is commercially available, in particular via Blücher GmbH, Erkrath/German Federal Republic, or Adsor-Tech GmbH, Premnitz/German Federal Republic.

In order to provide a wound dressing according to the invention with especially high efficacy of action, it can be provided according to the invention that the activated carbon is present in a quantity, in particular coating quantity, of 1 to 1,000 g/m$^2$, in particular 5 to 500 g/m$^2$, preferably 10 to 400 g/m$^2$, preferably 20 to 300 g/m$^2$ and especially preferably 25 to 250 g/m$^2$.

In order to ensure secure fixation of the activated carbon used and also protection against mechanical stress, it is preferred in the context of the present invention if the activated carbon is arranged on a planar, preferably textile support, preferably fastened or fixed thereon. Equally it can be provided that the activated carbon is arranged on a three-dimensional, preferably porous and/or textile support, preferably a foam or foamed substance, preferably fastened or fixed thereon or embedded therein. In this connection, it can in particular also be provided that the three-dimensional support is made on the basis of an elastomer resin or on the basis of a polyurethane.

The advantage of the aforesaid (support) materials can in particular be seen in that these are especially air permeable, which favors the healing process. As already mentioned above, the ventilation of the wound is of importance particularly as regards the supply of oxygen in the wound area and the prevention of the growth of anaerobic germs.

According to a particularly preferred embodiment of the present invention it can be provided that the activated carbon is arranged between a first textile fabric and a second textile fabric. Equally, it can be provided according to the invention that the activated carbon is present in the wound dressing so-to-speak in the form of a loose powder. In this connection, it can for example be provided that the powder is present or incorporated between a first textile fabric and a second textile fabric. Alternatively, the loose powder of the activated carbon can also be present between the hydrocolloid layer and an external covering layer. According to a further embodiment, it can further be provided that the activated carbon is incorporated into a textile fabric and is present in the wound dressing so-to-speak as an "activated carbon cushion", which contains activated carbon as a loose powder.

Furthermore, in the context of the present invention it can be provided that the first textile fabric and/or the second textile fabric is based on a fiber type selected from the group of polyesters (PES), polyolefins, in particular polyethylene (PE) and/or polypropylene (PP), polyvinyl chloride (PVC), polyvinylidene chloride (PVDC), cellulose acetate (CA), cellulose triacetate (CTA), polyacryl (PAN), polyamide (PA), polyvinyl alcohol (PVAL), polyurethanes (PU), polyvinyl esters, (meth-)acrylates, and mixtures thereof, in particular cellulose acetate and/or polyamide. The aforesaid fabrics are characterized in particular by their outstanding physiological compatibility, so that during use allergic and/or toxic reactions are in general not to be expected.

In addition, it is preferred according to the invention if the first textile fabric and/or the second textile fabric can at least essentially release no fibers and/or particles or at least essentially no activated carbon, so that the wound is not contaminated by the fiber material and no foreign bodies penetrate into the wound.

As regards the fixing of the activated carbon on or in the wound dressing according to the invention, in particular on the textile fabric, it is preferred according to the invention if the activated carbon is fixed on the first textile fabric and/or on the second textile fabric, in particular by means of a preferably medically and/or physiologically compatible adhesive. In this connection, it is further preferred if the adhesive is applied onto the first and/or second textile fabric discontinuously and/or in dots, so that good gas and air permeability of the fabric is ensured and also the activated carbon is not completely covered with adhesive and so still remains readily accessible.

As further regards the use of the adhesive, it is preferred if this is applied on the first and/or second textile fabric in a coating quantity of 1 to 100 $g/m^2$, in particular 5 to 50 $g/m^2$, preferably 10 to 40 $g/m^2$. Equally it can be preferred according to the invention that the adhesive covers the first and/or second textile fabric respectively at most 70%, in particular at most 60%, preferably at most 50%, preferably at most 40% and especially preferably at most 30%; in this way secure and stable fixing of the activated carbon is ensured with nonetheless good accessibility for the substances to be adsorbed and high gas and air permeability. Finally, the adhesive should be used in such a quantity and/or in such a condition that the surface of the activated carbon is at least 50%, in particular at least 60%, preferably at least 70% not covered with adhesive or is freely accessible; in this way, as previously stated, secure fixing or fastening of the activated carbon and high efficacy of the activated carbon are ensured.

Alternatively it can also be provided according to the invention that the activated carbon is present as a self-supporting layer, in particular as an activated carbon fiber sheet material or as a self-supporting, planar or three-dimensional, preferably continuous structure of mutually connected and/or mutually attached granular, in particular spherical, activated carbon particles.

It can also be provided in the context of the present invention that the activated carbon is embedded in the air permeable layer and/or adsorbed and/or fixed onto the air permeable layer.

In order to ensure adequate accessibility of the activated carbon for the substances to be adsorbed, it is further preferred according to the invention if the surface of the activated carbon is at least 50%, in particular at least 60%, preferably at least 70% freely accessible and/or is not covered. This is usually realized in the wound dressing according to the invention, irrespective of the form or layer in which the activated carbon is present.

As further regards the configuration according to the invention of the wound dressing, it is preferable if the individual layers of the wound dressing are each bonded to one another or if the individual layers of the wound dressing form a composite, so that during use and/or application of the wound dressing adequate stability is ensured.

In order further to improve the efficacy of the wound dressing according to the invention as regards the acceleration of wound healing and in addition to provide improved contamination protection, it can be provided according to the invention that the wound dressing further contains at least one active substance which can in particular be selected from the group of antimicrobially acting active substances, disinfecting active substances, inflammation-inhibiting substances, hemostyptic active substances and wound healing-promoting active substances.

Thus in this connection it is preferred according to the invention that the wound dressing is treated with at least one antimicrobial and/or disinfecting and/or inflammation-inhibiting and/or hemostyptic and/or wound healing-promoting active substance or that the wound dressing contains at least one antimicrobial and/or disinfecting and/or inflammation-inhibiting and/or hemostyptic and/or wound healing-promoting active substance. In this manner, reinforced protection of the wound to be treated against contamination, also in particular with regard to the commonly antibiotic-resistant hospital germs, is enabled. In addition, the wound healing can be actively promoted by the use of these active substances.

In this connection, it has been found particularly advantageous if the active substance has a biocidal or biostatic action, in particular a bactericidal or bacteriostatic and/or a fungicidal or fungistatic and/or virucidal or virostatic action. In this manner, the efficacy of the activated carbon can be still further increased.

As regards the active substances to be used as such, it has been found especially effective if the active substance is an antiseptic and/or a disinfectant.

A disinfectant is understood in particular to be chemical agents which serve to kill pathogenic organisms on organisms and objects. The spectrum of action of disinfectants in general comprises pathogenic microorganisms, in this connection including bacteria, viruses, spores, microfungi and moulds. As regards the term "antiseptic", this also describes germ-killing agents with which in particular wounds, skin and mucosae and medically used objects are treated, in order to achieve essential sterility. For further details on the terms "disinfectant" and "antiseptic", reference can be made to Römpp, Chemical Lexicon, $10^{th}$ Edition, Georg Thieme Verlag, Stuttgart/New York, keyword "disinfectant", pages 905 and 906 and keyword "antiseptic", page 132, and the literature cited therein, the whole content whereof relating to this is by reference included.

In this connection, it is preferred if the active substance, in particular the disinfectant, is selected from the group of polyhexamethylenebiguanide (polyhexanide), taurolidine, benzalkonium chloride, chlorhexidine, octenidine and physiologically compatible salts and derivatives thereof and mixtures thereof, preferably of octenidine and/or polyhexamethylenebiguanide (polyhexanide). The aforesaid active substances, in particular octenidine and polyhexanide, are especially well tolerated and have a broad spectrum of activity against many pathogens. Furthermore, in particular, side-effects, such as are associated with silver or other noble metals on use as bacteriostatic agents, can be prevented by the use of the aforesaid active substances. The additional use of a disinfectant is associated in particular with the advantage that, without wishing to be limited to this theory, the wound healing can be accelerated by a further reduction in the infection rate or by a decrease in bacterial attack.

The disinfectant octenidine used according to the invention can in particular be used in the form of the broad spectrum antiseptic octenidine dihydrochloride. Chemically speaking, octenidine belongs to the group of the quaternary ammonium compounds. During use on the skin, octenidine is characterized in particular by good tolerance, which minimizes the occurrence of side-effects. In addition, octenidine has an extremely broad spectrum of action, which includes both Gram positive and also Gram negative bacteria and also a large number of viruses and fungi. For further details on octenidine, reference can be made to Römpp, Chemical Lexicon, 10$^{th}$ Edition, Georg Thieme Verlag, Stuttgart/New York, page 2986, keyword "octenidine dihydrochloride", and the literature cited therein, the content whereof relating to this is by reference completely included herein.

According to a further preferred embodiment, in the context of the present invention polyhexanide can be used as the disinfectant. This is a disinfectant from the group of the biguanides, which in general have a hydrophobic backbone with several cationic biguanide groups, wherein the number of biguanide residues in the molecule is variable and influences the antimicrobial or bacteriostatic activity thereof. Polyhexanide and polyhexanide solutions are thus present in the form of mixtures based on polymers with different molecular weights. The number of biguanide residues per molecule generally lies in the range from 2 to 40. Here the individual biguanide residues are separated from each other by a hexamethylene chain.

Without wishing hereby to be limited to this theory, polyhexanide works on the basis of the protonation of the biguanide residues in the neutral pH range as a strong base. Through the strongly basic action, also without wishing hereby to be limited to this theory, the polyhexanide molecules enter into interaction with the negatively charged cell membrane of the pathogenic germs responsible by electrostatic interactions, which leads to destabilization or disintegration of the cell structures and can cause cell death.

Overall, polyhexanide has an extensive non-specific mode of action as a disinfectant, so that the growth even of germs difficult to inhibit, such as for example *Staphylococcus aureus, Bacillus subtilis, Pseudomonas aeruginosa* and *Escherichia coli*, can be efficiently inhibited. Furthermore, apart from the aforesaid antibacterial action, polyhexanide is also antivirally and antifungicidally active.

A further advantage which is associated with the use of polyhexanide is that because of the nonspecific mode of action, in contrast to antibiotics, in general no development of resistance results. In addition, with broad antimicrobial activity, polyhexanide is also characterized by outstanding tolerance and (tissue) compatibility, so that its use is also possible over a prolonged period.

Further, and not least, with chronic wounds because of the use of polyhexanide wound healing is accelerated in particular because of reduced bacterial attack and a reduced infection rate.

According to a further embodiment according to the invention, it can further be provided that the disinfectant, in particular polyhexanide, is used in the presence of at least one viscosity-increasing and/or matrix-forming substance, in particular based on an organic polymer, preferably a polyalkylene glycol, preferably polyethylene glycol and/or polypropylene glycol. Such a substance can in particular be the commercially available Macrogolum® 4000. Thereby the efficacy of action of the disinfectant can be further increased.

According to a further embodiment according to the invention, it can also be provided that the active substance is an active substance with a wound healing-promoting action, which can in particular be selected from the group of alginates, chitosan, hyaluronic acid and salts thereof, allantoin, beta-sitosterol, bromelain, dexpanthenol, pantothenic acid, urea, flavonoids, riboflavin, saponins, cineole, tocopherol and mixtures thereof.

The quantity of the active substance used can vary over wide ranges. In the context of the present invention it has been found that particularly good efficacy can be achieved with a quantity of active substance, in particular coating quantity, of 0.00001 to 5 g/cm$^2$, in particular 0.0001 to 2 g/cm$^2$, preferably 0.001 to 1 g/cm$^2$ and especially preferably 0.01 to 0.5 g/cm$^2$.

According to one embodiment of the present invention, it can be provided that the active substance is present in the air permeable layer and/or in the activated carbon, in particular in the activated carbon-containing layer. Equally, it can be provided that the active substance is present in the air permeable layer and in the activated carbon, in particular in the activated carbon-containing layer.

The active substance can at times be incorporated either only in the air permeable layer or alternatively only in the activated carbon, in particular in the activated carbon containing-layer. The introduction of the active substance into the air permeable layer has the result that direct or unmediated release of the active substance from the foam layer into the wound takes place, while the introduction of the active substance into the activated carbon, in particular into the activated carbon-containing layer, is associated with the advantage that the active substance present in the activated carbon is released slowly or over a prolonged period or released at the wound (i.e. so-to-speak a depot action is achieved).

The incorporation of the active substance both into the foam layer and also into the activated carbon, in particular into the activated carbon-containing layer, is preferred according to the invention. This embodiment is in particular associated with the advantage that in this manner so-to-speak a double action can be created, since the release of the active substance from the air permeable layer takes place directly or unmediated into the wound, while on the other hand the active substances present in the activated carbon, in particular in the activated carbon-containing layer, are released with retardation or slowly, whereby treatment of the wound with the particular active substance can be assured over a prolonged period with controlled release.

In principle however, it is also possible to introduce the active substance, at least partially, into layers of the wound dressing according to the invention other than the activated carbon-containing layer or the layer containing the hydrocolloid, preferably collagen, insofar as such layers are present (e.g. in the optional textile supports or support layers etc.). Furthermore, it is also possible to provide one or more separate or additional layers specifically for the introduction of the active substance or substances.

As regards the introduction of the active substance or substances into the air permeable layer, these can be incorporated directly into the solution or dispersion of at least one hydrocolloid and/or organic polymer during the production of the foam layer.

The introduction of the active substance into the activated carbon or into the activated carbon-containing layer can in particular be effected by contacting, preferably impregnating, the activated carbon with the active substance or an active substance solution.

As regards the linguistic formulation "that the active substance is present in the air permeable layer, and/or in the activated carbon, in particular in the activated carbon-containing layer", this is to be understood in particular to mean that the active substance is introduced or incorporated into the particular layer, in particular fixed in or on the particular layer, preferably reversibly fixed, and thus is preferably released again on contact with the wound or with water or moisture or released into the wound.

In addition, according to a particular embodiment of the present invention it can be provided that the wound dressing is treated with at least one substance which possesses protease activity. Here also it can be provided that the substance with protease activity is present in the hydrocolloid layer or collagen layer and/or in the layer equipped with activated carbon. Through the purpose-directed use in particular of small quantities of a substance with protease activity, it is possible to decrease the need for a debridement.

Figure 2:
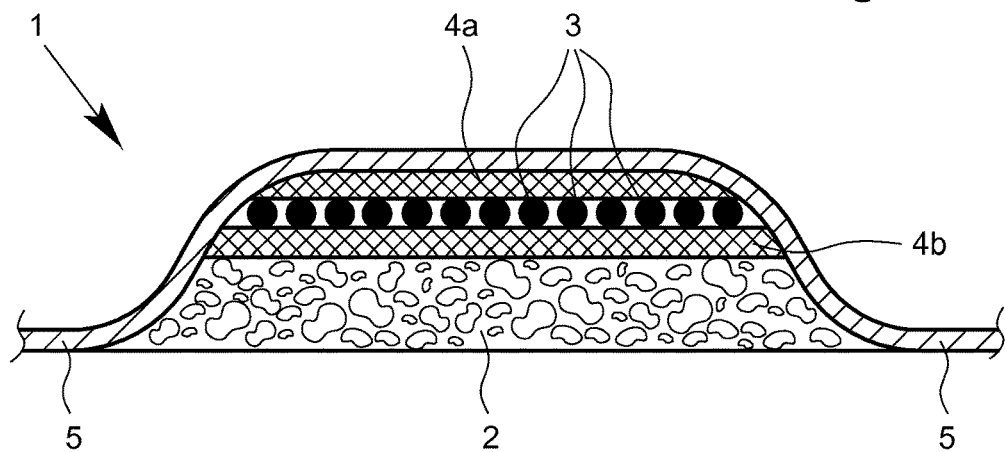
Figure 3:
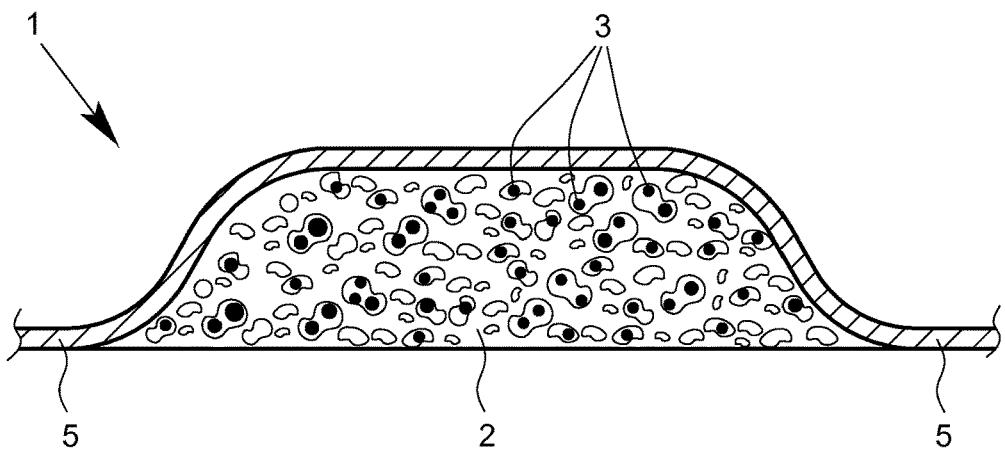

Further advantages, properties and features of the present invention follow from the following description of preferred practical examples shown in the drawings:

FIG. 1 shows a schematic cross-section through the layer structure of a wound dressing according to a first preferred practical example of the present invention corresponding to a specific embodiment, FIG. 2 shows a schematic cross-section through the layer structure of a wound dressing according to a further preferred practical example of the present invention corresponding to a further specific embodiment, and FIG. 3 shows a schematic cross-section through the layer structure of a wound dressing according to a further preferred practical example of the present invention corresponding to a further specific embodiment.

FIG. 1 shows a schematic cross-section through the layer structure of a wound dressing 1 corresponding to a specific configuration of the present invention. The wound dressing 1 according to the invention, suitable in particular for therapeutic wound care, has an activated carbon 3 and an air permeable layer 2, where in the use condition the air permeable layer 2 is the layer facing the wound. According to the practical example shown, the wound dressing 1 can have an adhesive border 5, which firstly enables fixing of the wound dressing 1 during its use in particular on the skin and secondly also holds together the individual layers 2 and 3. In order to ensure adequate stability of the wound dressing 1 according to the invention, the layers described above are advantageously made as a composite, wherein the layers can for example be bonded preferably discontinuously with the active substances cited above.

FIG. 2 shows a schematic cross-section through the layer structure of a wound dressing 1 corresponding to a further specific configuration. The wound dressing 1 according to the invention, which is suitable in particular for therapeutic wound care, contains an activated carbon 3, wherein the activated carbon is fixed between two textile support materials 4a and 4b, in particular fixed onto each of them, and the textile support material 4b forms a first outer layer of the wound dressing 1. Furthermore, the wound dressing 1 according to the invention has an air permeable layer 2 which is the second outer layer of the wound dressing 1 according to the invention, and in the use condition the air permeable layer 2 is the layer facing the wound. In order to ensure adequate stability of the wound dressing 1 according to the invention, the layers described above are advantageously made as a composite. According to the practical example shown, the wound dressing 1 can have an adhesive border 5, which enables fixing of the wound dressing 1 during its use in particular on the skin.

FIG. 3 shows a schematic cross-section through the layer structure of a wound dressing 1 corresponding to a third specific configuration. The wound dressing 1 according to the invention, which is suitable in particular for therapeutic wound care, contains an activated carbon 3 and an air permeable layer 2, wherein the activated carbon 3 is introduced into the air permeable layer 2 or fixed thereon. In particular, the activated carbon 3 is fixed in the pore system of the air permeable layer 2. According to the practical example shown, the wound dressing 1 can have an adhesive border 5, which enables fixing of the wound dressing 1 during its use in particular on the skin.

Hence in the context of the present invention a wound dressing with biocidal and/or biostatic, in particular antimicrobial and wound healing-promoting properties is provided, wherein the aforesaid properties are in particular also ensured by a biostatically or biocidally, in particular antimicrobially active activated carbon. As well as the binding of odorous substances and toxins, the activated carbon can inactivate or kill pathogens (such as for example fungi, bacteria and viruses), since these also adhere to the activated carbon. In this manner, the bacterial load or the microbial count in wounds is effectively and permanently minimized. Owing to the outstanding biocidal or biostatic, in particular antimicrobial, properties of the activated carbon, the concentration of other antimicrobially active agents can be reduced or their use entirely eliminated, which correspondingly leads to a decrease in the toxicological potential of the wound dressing. Overall, wound healing is promoted in particular by the binding of toxins, by the exudate management for maintenance of the moist-warm conditions optimal for wound healing and by effective gas exchange. In addition, the efficacy can be further increased or optimized by also integrating still further (active) substances, e.g. wound healing-promoting substances, into the wound dressing; however because of the outstanding properties of the activated carbon as such, the quantities optionally to be used for this are markedly smaller compared to the quantities necessary in the state of the art, so that the tolerance of the wound dressing according to the invention is considerably better.

The present invention thus in particular provides a wound dressing with a biocidal or biostatic, in particular antimicrobial, activated carbon; the latter, optionally even without additional use of an antimicrobially active agent, as well as the adsorption of toxins and odorous substances is also capable of permanently inactivating or killing pathogens (e.g. fungi, bacteria and viruses). Because of this, the toxicological risk which would be necessary through the use of high concentrations of antimicrobial substances according to the state of the art in order to provide effective contamination protection can be decreased. In addition, wound healing is promoted, since the use of the activated carbon enables cleansing of the exudate by adsorption of toxins. Further, the activated carbon so-to-speak acts as a sorbent store for the exudate, so that this can be absorbed to maintain a moist, but not wet, wound environment, but can also be released again into the wound. In addition, the specific release of additional active substances from the activated carbon is possible. Through good gas exchange via the wound dressing, the wound healing processes are further accelerated.

The activated carbon with biostatic or biocidal, in particular antimicrobial, properties used according to the invention is thus capable firstly of binding toxins and odorous substances and secondly also acting as a protection against contamination.

The mode of action of the activated carbon is now described in still more detail below, but the following explanations are not intended to limit the present invention in any way:

The activated carbon is capable of killing or permanently inactivating pathogens (e.g. fungi, bacteria and viruses), since these adhere to it and are thus immobilized. The inability to move or immobilization thus created prevents the proliferation of the pathogens; further, nutrients are withdrawn from some pathogens owing to the strong attractive forces of the activated carbon, and likewise become immobilized and are no longer available for the pathogens. Further, because of the strong interactions, the activated carbon causes damage to the cell membrane and the cell wall of the pathogens.

The outstanding adsorptent capacity of the activated carbon is due in particular to the textural properties of its (internal) surface, in particular to electro-static interactions and Van der Waals forces. Said effects cause a long-term reduction in the bacterial load or microbial count in the wound and as a result a minimization of the contamination risk.

As already stated above, the biostatically or biocidally, in particular antimicrobially active activated carbon can be contained in one or more layer(s) of the wound dressing. According to a particular embodiment of the present invention, the activated carbon can be present separately in the wound dressing e.g. as a finishing agent on a textile fabric. In addition, the textile fabric can be deliberately used for modulation or adjustment of gas and liquid permeability via the choice of the polymers or of the filaments, fibers and yarns arising therefrom. This is of particular importance with regard to the various wound healing stages, since these sometimes impose different requirements for the moisture content and the gas composition.

According to a further embodiment of the present invention, it can be provided that the activated carbon in the form of a cushion is completely enveloped by a textile fabric and fixed thereto with an adhesive. Release of the activated carbon is thereby prevented.

In this connection, by use of a textile fabric in the form of a knit it can be ensured that the wound dressing is more permeable and that pathogens reach the antimicrobially active activated carbon with the wound exudate. Alternatively, nonwovens or wovens can also be used. If the textile fabric comes directly into contact with the injury, according to the invention a yarn not adhering to the wound is used so as to avoid injuries during dressing changes. Such a layer can be treated with substances of various types which are important for the healing process and are such as were explicitly cited above. In a particular embodiment of the invention, it is a layer containing wound healing-promoting substances such as for example alginate, chitosan or hyaluronic acid. Also possible however, is the addition of other substances such as for example allantoin, beta-sitosterol, urea, bromelain, dexpanthenol, flavonoids, riboflavin, saponin, cineole, tocopherol and other substances of this nature.

According to a particular embodiment of the present invention, it can further be provided that the textile fabric adheres to a layer of absorbable hydrocolloid, in particular collagen, which in this connection fulfils several functions: because of its foamy soft structure, irregularities are smoothed out by such a collagen layer. In addition, the gap between the wound and the antimicrobially active activated carbon is decreased, which increases its efficacy. Besides this, a high capillary activity results from the pore structure of the collagen matrix, which enables the uptake and transport of large volumes of liquid, in particular wound fluids. Because of this, a moist wound environment is provided, which prevents maceration detrimental to the wound healing. In addition, the exudate flow out of the wound and onwards to the activated carbon is ensured and excess moisture is released in the form of water vapor. Impurities, proteases and free radicals are bound both by the activated carbon and also by such a collagen layer in a different manner and removed from the wound.

Further, the biostatically or biocidally, in particular antimicrobially active properties of the activated carbon prevent the formation of a biofilm or a bacterial layer and enable a stable, long-persisting wound exudate cleansing process. Were a biofilm to form, this would also be detrimental to the wound healing since contact of the liquid with the activated carbon would be prevented and gas exchange in this way prevented. Since the biostatic or biocidal, in particular antimicrobial action is provided by the activated carbon as such, the creation of contamination protection by decreased oxygen supply, such as must however often be effected in the state of the art, is also not necessary. The increased gas exchange in the context of the present invention and the improved exudate management overall ensure improved wound healing.

According to a further embodiment, the wound dressing according to the invention can contain an additional, in particular antimicrobial active substance in order to support the mode of action of the activated carbon synergistically. This can in particular be polyhexamethylenebiguanide (PHMB), chlorhexidine or octenidine, but any other antiseptic and/or disinfectant, such as for example chitosan or triclosan, can also be used.

If an especially strong antimicrobial action is to be achieved, such as for example in the case of an infection with several bacterial strains, it can also be provided that the wound dressing be treated with antibiotics. In the context of the use of the wound dressing, the particular active substance is released from the wound dressing, diffuses into the wound and exerts its activity in the whole wound area. This also enables inactivation of microorganisms in deepened wound areas. However, the activated carbon used according to the invention ensures that even in case of complete release of the active substance from the wound dressing, the biostatic or biocidal, in particular antimicrobial, action is still always sufficient to prevent recontamination of the wound. This is a problem previously unsolved in the state of the art.

In this connection, by means of the wound dressing according to the invention it is in particular possible to lower the concentration of biostatic or biocidal, in particular antimicrobial, substances to be used compared to the state of the art or to dispense with them entirely and consequently to achieve minimization of the toxicological risk or of side-effects related thereto. Further, no pathogens can enter the wound from outside, since the activated carbon layer is impassable to them.

Furthermore, it can be provided according to the invention that the wound dressing additionally also contains analgesic or painkilling active substances. These can be anti-inflammatory substances, such as for example ibuprofen and diclofenac, and painkilling substances, such as for example lidocaine and procaine.

It is also possible for the wound dressing to contain a styptic (hemostyptic) active substance. One or more specifically local as well as systemically active hemo-styptic agents are possible. An especially preferred modification concerns the use of hydrophilic, high molecular weight polymers, such as for example cellulose derivatives, which promote hemostasis by contact activation of the endogenous clotting system. Further, these agents enable wound bed adaptation and simultaneously function as adhesives which in turn favors the adhesion of the wound dressing.

The aforesaid active substances can themselves form an independent layer, but can also be integrated or incorporated into one or more layer(s) of the wound dressing. Further, the structure of the wound dressing, the particular active substance concentrations and particle sizes used and the nature of the binding of the active substances in the individual layers influence their solubility behavior. Accordingly, targeted timed release at various phases of the wound healing is possible.

In a further preferred embodiment, the fixing of the wound dressing in the use condition is reinforced by an adhesive border. This is in particular an adhesive area, such as can for example be located on the textile fabrics between which the activated carbon can be arranged or fixed and which so-to-speak form a kind of "activated carbon cushion". The adhesive area extends beyond the edges of the "activated carbon cushion" and ensures an adhesive border, so that the wound dressing can in this way be stably fixed on the patient's skin. It is also possible according to the invention to integrate a barrier or linen-protecting layer into this area. As adhesives in the present invention in a wound dressing according to the invention, in particular substances such as for example polyacrylate, siloxane or polyisobutadiene are used. Through such an adhesive layer, the use of a secondary bandage or film adhesive can be dispensed with. In addition, side sealing is ensured. Further, neither the wound nor the surrounding skin are torn with the use of a previously described adhesive border or such an adhesive layer. The risk of incorrect application is also minimized through the adhesive border. In particular, it can be provided according to the invention that the wound dressing is equipped with at least one adhesive, barrier and/or linen-protecting layer.

In order further to improve applicability, it can also be provided that the individual layers are colored or their surface structured for identification.

Hence, as a result, in the context of the present invention an efficient wound dressing with improved wound healing profile is provided.

A further subject of the present invention is, according to a second aspect of the present invention, the use of a wound dressing as described herein for the therapeutic, in particular topical, wound care of the human or animal body, in particular for the therapeutic, preferably topical, treatment of wounds and/or tissue breaks.

As regards the term "wounds" or "tissue breaks", for the avoidance of unnecessary repetitions, reference is made to the explanations and definitions mentioned in the context of introduction to the specification.

In particular in the context of the present invention these are understood to mean all classes or types of wounds, as also cited in the introductory section. Mechanical wounds are understood in particular to be piercing, cutting, crushing, laceration, scratch and abrasion wounds. Those tissue breaks in particular which are caused by the action of extreme cold or heat belong to the class of thermal wounds. In contrast, chemical wounds are understood to be those triggered by the action of chemical substances, in particular by erosion by acids or alkalis. Radiation wounds occur in particular through the action of actinic or ionizing radiation. In addition, the wound can be present in physiological conditions which place especially high requirements on the treatment or therapy. Thus in necrotizing wounds detachment of the cell layers and tissue death occurs. It is also possible that wounds become infected by pathogens such as bacteria, fungi or viruses. Furthermore, a wound which is still not completely healed after a period of about eight weeks is defined as a chronic wound. For example, on the one hand pressure ulcers, such as often occur in bedridden patients, and on the other wounds such as are often associated with circulatory disorders, e.g. type 2 diabetes mellitus or chronic venous insufficiency, are described as chronic wounds.

According to the invention, it is for example possible to use the wound dressing according to the invention for the therapeutic treatment of mechanical wounds, in particular cutting, piercing, crushing, laceration, scratch and/or abrasion wounds.

Use of the wound dressing according to the invention for the therapeutic treatment of thermal wounds, in particular wounds triggered by cold or heat burns, is also possible.

Further, it can be provided that the wound dressing according to the invention is used for the therapeutic treatment of chemical wounds, in particular wounds triggered by erosion with alkalis and/or acids.

According to the invention, it can in particular be provided that the wound dressing is used for the therapeutic treatment of necrotizing and/or infected and/or chronic wounds.

Equally, it can also be provided according to the invention that the wound dressing according to the invention is used for the therapeutic treatment of acute wounds.

Finally, it can equally be provided according to the invention to use the wound dressing according to the invention for the therapeutic treatment of pressure ulcers and/or wounds triggered by circulatory disorders.

For the avoidance of unnecessary repetitions, for further details on this aspect of the invention reference can be made to the above explanations on the first aspect of the invention, which correspondingly apply with regard to this aspect of the invention.

Further configurations, adaptations and variations and advantages of the present invention are instantly recognizable and realizable for those skilled in the art on reading the description, without them thereby departing from the scope of the present invention.

The present invention is illustrated on the basis of the following examples, which however in no way limit the present invention.

EXAMPLES

1. Preparation of Wound Dressings According to the Invention and not According to the Invention In order to compare the wound dressing according to the invention with wound dressings not according to the invention, various embodiments of the wound dressings according to the invention and comparison wound dressings were prepared:

The wound dressings according to the invention here had the following characteristics:
  the wound dressings A and A' each had a collagen layer and an activated carbon layer arranged between two polyamide-based textile fabrics, the wound dressings B and B' likewise each had a collagen layer and an activated carbon layer arranged between two polyamide-based textile support materials and in addition both collagen layer and also activated carbon layer were treated with octenidine, and the wound dressing C likewise had a collagen layer and an activated carbon layer arranged between two polyamide-based textile support materials and in addition both collagen layer and also activated carbon layer were treated with polyhexanide.

Meanwhile, the other wound dressings had the following properties:

wound dressing D was based on a standard activated carbon nonwoven;

wound dressing E was based on a polyhexanide-impregnated polyurethane foam; and wound dressing F was based exclusively on collagen foam.

The collagen layer of each of the wound dressings was produced starting from an aqueous collagen suspension with subsequent lyophilization on a suitable support, whereby a corresponding collagen foam resulted. Porcine skin-based collagen was used.

As the activated carbon for each of the wound dressings A, B and C, a spherical activated carbon from Adsor-Tech GmbH, Premnitz/Federal German Republic was used, wherein the activated carbon was obtained by carbonization and subsequent activation of organic polymers based on polystyrene, in particular divinylbenzene-crosslinked polystyrene (absolute particle size: ca. 0.2 to 0.6 mm, micropore content: ca. 76%, BET surface area: ca. 1.775 $m^2/g$, total pore volume as per Gurvich: ca. 2.2 $m^2/g$, pressure/burst strength: >15 Newtons/activated carbon sphere, fractal dimension of the open porosity: 2.55, abrasion resistance: 100%).

As the activated carbon for each of the wound dressings A' and B', a normal commercial phenolic resin-based activated carbon was used (absolute particle size: ca. 0.2 to 0.6 mm, micropore content: ca. 57%, BET surface area: ca. 1.375 $m^2/g$, total pore volume as per Gurvich: ca. 1.5 $m^2/g$, pressure/burst strength: <10 Newtons/activated carbon sphere, fractal dimension of the open porosity: 2.15, abrasion resistance: 87%).

2. In Vitro Studies on the Wound Dressings According to the Invention

In order to test the efficacy of the various wound dressings against hospital germs, which are a drastic problem in particular with chronic wounds, the antimicrobial performance of the wound dressings was studied in the context of an inhibition zone test.

The inhibitor testing performed was performed in the context of a test modified after Bauer-Kirby (DIN 58940-3). In the context of the test, the extent to which the wound dressings are capable of inhibiting the growth of the hospital germs *Staphylococcus aureus, Staphylococcus epidermidis, Escherichia coli, Pseudomonas aeruginosa* and *Proteus mirabilis* on solid media was investigated.

For this, after completion of the incubation time of the test strains, the area [$mm^2$] of the inhibition zone, i.e. the region wherein no bacterial growth had taken place, was measured and assessed as a measure of the antimicrobial efficacy of the wound dressing concerned.

The inhibitor testing was performed on solid media based on blood agar containing 5 wt. % sheep blood. Before inoculation of the solid medium, dilutions of the test germs were each prepared such that countable colony-forming units were formed on the blood plates.

The respective dilutions of the test germ suspensions were plated out under sterile conditions. Next, the wound dressings were aseptically cut with a scalpel into 1 cm×1 cm sized pieces, laid on the culture plates under sterile conditions and removed again after hours contact time. Aerobic culturing at 37° C. followed. The area of the inhibition zone around each of the wound dressings was digitally measured after 48 hours total incubation time. The assessment was then performed by comparison of the inhibition zones formed around each wound dressing.

In the context of the inhibitor testing, the growth of the hospital germs *Staphylococcus aureus, Staphylococcus epidermidis, Escherichia coli, Pseudomonas aeruginosa* and *Proteus mirabilis* could be outstandingly inhibited with all the wound dressings according to the invention. The strongest growth inhibition was achieved with use of the wound dressing C according to the invention, which further contained polyhexanide as an antimicrobial active substance. Outstanding results were also achieved with use of the wound dressings B and B', which instead of polyhexanide contained octenidine as the antimicrobial active substance. With the wound dressings A and A' according to the invention which were based on a combination of collagen foam and activated carbon, the growth of the microorganisms listed above could also be satisfactorily inhibited in the context of the inhibitor testing, less efficiently however than with the wound dressings B, B' and C.

In contrast, with the comparison wound dressings D, E and F, no such efficient and satisfactory inhibition of the growth of the aforesaid germs could be observed.

As regards the wound dressings according to the invention, in the context of the inhibition zone tests performed by the applicant, it could in particular be shown that the use of specific activated carbons leads to an efficient additional increase in the activity of wound dressings based on activated carbon and collagen foam as regards inhibition of growth of hospital germs, which can be still further increased by the use of an additional antimicrobial active substance.

The results concerning this are explained in detail below:

A comparison of the results for the inhibitor testing of the wound dressings A and A' according to the invention with no additional disinfectant with those of the wound dressing B, B' and C according to the invention, which each contained an additional disinfectant, show that through the combination of activated carbon and collagen on the one hand with a further active substance with disinfecting action on the other, the growth of microorganisms can be inhibited particularly effectively. With each of the wound dressings A and A', a satisfactory inhibition of microbial growth was achieved, however the use of the wound dressings B, B' and C, which additionally contained octenidine or polyhexanide resulted overall in significantly larger inhibition zones.

As regards the action of the activated carbon, the comparison of the wound dressings A and B respectively with the wound dressings A' and B' shows that in particular activated carbons based on polystyrene with a high microporosity, a large BET surface area and a large fractal dimension of the open porosity, such as is in particular marketed by Adsor-Tech GmbH, have particularly good antimicrobial properties. For with the wound dressings A and B, compared to the wound dressings A' and B' respectively, which each contained a normal commercial phenolic resin-based activated carbon with lower microporosity, smaller BET surface area and a lower value for the fractal dimension of the open porosity, significantly larger inhibition zones could be created in the context of the inhibition zone test.

In addition, the values determined in the context of the inhibition zone test for the respective wound dressings and the germs used can be obtained from Table 1.

TABLE 1

Results of the inhibition zone test

| | Test germ | Inhibition zone [mm$^2$] |
|---|---|---|
| Wound dressing A | Pseudomonas aeruginosa | 92 |
| | Staphylococcus aureus | 254 |
| | Staphylococcus epidermidis | 241 |
| | Escherichia coli | 83 |
| | Proteus mirabilis | 56 |
| Wound dressing A' | Pseudomonas aeruginosa | 85 |
| | Staphylococcus aureus | 205 |
| | Staphylococcus epidermidis | 199 |
| | Escherichia coli | 87 |
| | Proteus mirabilis | 41 |
| Wound dressing B | Pseudomonas aeruginosa | 124 |
| | Staphylococcus aureus | 371 |
| | Staphylococcus epidermidis | 340 |
| | Escherichia coli | 243 |
| | Proteus mirabilis | 112 |
| Wound dressing B' | Pseudomonas aeruginosa | 104 |
| | Staphylococcus aureus | 339 |
| | Staphylococcus epidermidis | 327 |
| | Escherichia coli | 238 |
| | Proteus mirabilis | 95 |
| Wound dressing C | Pseudomonas aeruginosa | 137 |
| | Staphylococcus aureus | 397 |
| | Staphylococcus epidermidis | 373 |
| | Escherichia coli | 289 |
| | Proteus mirabilis | 119 |
| Wound dressing D | Pseudomonas aeruginosa | 79 |
| | Staphylococcus aureus | 152 |
| | Staphylococcus epidermidis | 176 |
| | Escherichia coli | 76 |
| | Proteus mirabilis | 19 |
| Wound dressing E | Pseudomonas aeruginosa | 82 |
| | Staphylococcus aureus | 191 |
| | Staphylococcus epidermidis | 182 |
| | Escherichia coli | 81 |
| | Proteus mirabilis | 34 |
| Wound dressing F | Pseudomonas aeruginosa | 69 |
| | Staphylococcus aureus | 112 |
| | Staphylococcus epidermidis | 107 |
| | Escherichia coli | 56 |
| | Proteus mirabilis | 0 |

Overall, it follows from the above results that the growth of microorganisms can be markedly more strongly inhibited with a combination of collagen and activated carbon compared to state of the art wound dressings. In addition, it becomes clear that this effect can be further increased by a) the use of a further disinfecting active substance and b) the use of specific activated carbons.

The especial advantage of the wound dressings according to the invention is also in particular to be seen in that through their use the growth of microorganisms which are known for the occurrence of antibiotic resistance, in particular the so-called hospital germs, can also be inhibited.

3. Use and Efficacy Studies

In order to compare the efficacy of the wound dressings according to the invention with the wound dressings not according to the invention, test subjects aged from 70 to 85 who were suffering from chronic or necrotizing wounds were treated with either over a period of four weeks. For this, the respective wound dressing was applied onto the affected part of the body. Within the first week of the treatment period, the wound dressing was changed in the morning and evening; beyond the second week, changing of the wound dressing was effected on the basis of the condition of the wound concerned. The further the wound healing had progressed, the longer was the period between the dressing changes, but in all cases a dressing change was performed after two days at the latest.

In the context of the studies performed, a test subject group of 15 persons was studied for each of the wound dressings A and B. 15 persons, of whom 11 were female and 4 male, received the wound dressing A which was based on a combination of activated carbon and collagen. A further 15 persons, of whom 8 were female and 7 male, for improvement of the wound healing of their chronic wounds received the wound dressing B, which was treated with the antimicrobial active substance octenidine both in the collagen layer and also in the activated carbon layer.

After four weeks' therapy or treatment of the chronic wounds, a marked improvement could be discerned in all test subjects. The wound secretion and inflammatory symptoms had completely abated and in all the test subjects the periwound area was intact after the treatment. Overall, after the four weeks' therapy, the wounds were completely closed and largely epithelized in 9 test subjects in the first group (wound dressing A) and after three weeks' therapy in 13 test subjects in the second group (wound dressing B). In the other test subjects, the wounds were sometimes not yet completely closed, however the wound bed appeared pink and granulating and the periwound area was intact, which indicates speedy healing of the wound. On the basis of the assessment of the condition of the wounds after three and four weeks respectively, overall a satisfactory result could be noted as regards healing progress in the chronic wounds. As regards the efficacy of wound dressings A and B, the additional treatment of the wound dressing with an antimicrobial active substance such as octenidine accelerates the wound healing. In particular, in the test subjects treated with the wound dressing B, a more rapid regression of the inflammatory symptoms could be observed, especially when infections were present.

As regards the wound dressings D, E and F, a test subject group was also studied, with the treatment period being four weeks for each. From the test subject group, 15 persons, of whom 8 were female and 7 male, received wound dressing D. A further 15 test subjects, of whom 6 were female and 9 male, were treated with the wound dressing E. And a further 15 test subjects, of whom 9 were female and 6 male, were treated with the wound dressing F.

In the test subjects treated with the wound dressing D, an improvement in the wound healing was observed in the treatment period, however closure or complete epithelization of the wound could only be observed in 5 of the total of 15 test subjects; in the other 10 test subjects, the wounds were not yet completely closed, but at least had a granulating wound bed.

As regards the odor adsorption of the wound dressing D however, this was largely satisfactory. In addition, in 8 of the total of 15 test subjects, slight to moderate inflammatory reactions or wound infections occurred, which rendered additional therapy with antimicrobial substances necessary. Thus overall, compared with the wound dressings A and B, optimal protection against contamination with pathogenic germs cannot be achieved with the wound dressing D. In particular, the lesser contamination protection also results in delayed wound healing.

With the wound dressing E, results comparable with the wound dressings A and B also could not be achieved. Only in 2 of the 15 test subjects who were treated with wound dressing E was the wound completely closed and epithelized. In a total of 8 of the 15 test subjects, the wound bed appeared pink and granulating, which indicates progression of the healing process. In 2 test subjects, the wound bed was still coated with fibrin, which is a characteristic of the early phases of the healing process. In addition, the wound had become infected in 2 of the 15 test subjects, so that severe inflammatory symptoms at times arose. Overall, wound dressings based on polyurethane foam which had been impregnated with a disinfectant offer neither optimal contamination protection nor satisfactory odor adsorption.

With the exclusively collagen-based wound dressing F, the worst results were obtained. Only in one of the test subjects was the wound completely closed and epithelized; the wound bed appeared pink and granulating in only 4 test subjects, and in 10 test subjects the wound bed was still coated with fibrin. In addition, the test subjects complained of the inadequate odor adsorption. Thus it was found that exclusively collagen-based wound dressings result neither in accelerated wound healing nor in adequate odor adsorption.

The wound dressings tested were assessed according to a school grading system, i.e. with assessments varying in the range from 1=very good to 6=insufficient, as regards acceleration of wound healing, contamination protection and control of infection and inflammation symptoms as well as odor adsorption. The results concerning this for the wound dressings tested can be obtained from table 2 below:

TABLE 2

Assessment of the wound dressings with the school grading system

|  | Acceleration of wound healing | Contamination protection/control of infection and inflammation symptoms | Odor adsorption |
| --- | --- | --- | --- |
| Wound dressing A | 1.9 ± 0.2 | 2.2 ± 0.1 | 1.6 ± 0.3 |
| Wound dressing B | 1.8 ± 0.1 | 1.7 ± 0.2 | 1.7 ± 0.4 |
| Wound dressing D | 3.5 ± 0.3 | 3.1 ± 0.2 | 2.0 ± 0.3 |
| Wound dressing E | 3.2 ± 0.5 | 2.7 ± 0.1 | 3.5 ± 0.2 |
| Wound dressing F | 4.3 ± 0.3 | 3.8 ± 0.2 | 3.4 ± 0.2 |

The use and efficacy observations made demonstrate the outstanding efficacy of the wound dressings A and B in the treatment of chronic wounds, in particular in connection with pressure ulcers and wounds which are connected in the context of underlying diseases associated with circulatory disorders.

From the results, it follows clearly that through the combined use of activated carbon on the one hand and collagen on the other, wound healing can be significantly accelerated and in addition inflammatory symptoms and infections can be alleviated. Furthermore, through use of the activated carbon-containing wound dressings it is possible to adsorb unpleasant odors such as often arise in connection with chronic wounds.

The best results overall were achieved with the wound dressings A and B, with wound dressing B, which as well as activated carbon and collagen was treated with the bactericidal component octenidine, yielding the best results. Through the additional treatment with a disinfecting or bactericidal active substance, inflammatory symptoms could be still better controlled and there was improved contamination protection, so that overall the healing process could also be still further accelerated.

Table 3 shows a comparison of the basic properties of the wound dressings according to the invention on the one hand with those of the wound dressings of the state of the art on the other, as described in section 1).

TABLE 3

Properties of wound dressings according to the invention and not according to the invention

| Parameter | Wound Dressing | | | |
| --- | --- | --- | --- | --- |
|  | wound dressings according to the invention (A, A', B, B' and C) | wound dressing with a normal commercial activated carbon (D) | polyurethane foam impregnated with polyhexanide (E) | collagen foam (F) |
| Description of wound dressing | wound dressings according to the invention A to C described above | textile support based on a viscose/polyamide mixture with activated carbon layer lying between them | foam dressing of polyurethane wherein the polyurethane was impregnated with polyhexanide | absorbable collagen foam wound dressing |
| Antimicrobial or biocidal properties | very high | not present | detectable but not for all test germs | very low, hardly detectable |
| Adsorption of germs and components of germs from the wound | strong | weak | weak | weak |
| Promotion of wound healing | very strong | weak | weak | strong |
| Initiation of wound healing in stagnating wounds | strong | not present | not present | weak |
| Spatial adaptation to the wound | very strong | weak | moderate | strong |

TABLE 3-continued

Properties of wound dressings according to the invention and not according to the invention

| Parameter | Wound Dressing | | | |
| --- | --- | --- | --- | --- |
| | wound dressings according to the invention (A, A', B, B' and C) | wound dressing with a normal commercial activated carbon (D) | polyurethane foam impregnated with polyhexanide (E) | collagen foam (F) |
| Protection against maceration | strong | weak | moderate | moderate |
| Exudate management | strong | weak | weak | moderate |
| Gas permeability | very strong | strong | weak | strong |
| Odor and toxin adsorption | strong | moderate | weak | weak |
| Barrier action against outside influences | very strong | moderate | strong | moderate |
| Cooling effect | very strong | weak | weak | strong |
| Dressing change | painfree | painful | painful | largely painfree |
| Toxicological risks | low, since the polyhexanide quantity necessary is reduced | low | elevated owing to relatively large quantities of polyhexanide | low |

4. Summary

Overall, it is clear from the practical examples that the wound dressings according to the invention are improved in many ways compared to wound dressings not according to the invention, in particular through the biostatic or biocidal treatment or properties and/or through the combination of activated carbon on the one hand and collagen on the other. Thus with use of the wound dressings according to the invention for therapeutic wound care, the wound healing process is significantly accelerated. In addition, there is excellent contamination protection, in particular against hospital germs, which are often resistant to antibiotics and the occurrence whereof in the wound area places exceptional requirements on the therapy. Further, the wound dressings according to the invention have good odor adsorption properties, which is above all beneficial to the patients' wellbeing.

The invention claimed is:

1. A wound dressing for therapeutic wound care,
wherein the wound dressing has a multilayer structure, wherein the multilayer structure comprises at least one air permeable layer with a porous or foam-based structure and at least one layer comprising activated carbon,
wherein the air permeable layer without cavities or intervening spaces forms an outer layer of the wound dressing and wherein the wound dressing is adapted to be applied to a wound with the air permeable layer arranged on a side of the wound dressing facing the wound,
wherein the air permeable layer is formed by a hydrocolloid foam wherein the hydrocolloid is collagen,
wherein the air permeable layer has a compressive hardness in the range from 5 to 50 kPa,
wherein the activated carbon comprises granular activated carbon,
wherein the wound dressing as a whole is made air permeable with an air permeability of at least 25 $l \cdot m^{-2} \cdot sec^{-1}$ and up to 10,000 $l \cdot m^{-2} \cdot sec^{-1}$ at a flow resistance of 127 Pa, and
wherein the air permeable layer has a thickness in the range of from 0.01 to 100 mm and makes up 5% to 95% of the total thickness of the wound dressing.

2. A wound dressing for therapeutic wound care,
wherein the wound dressing has a multilayer structure, wherein the multilayer structure comprises at least one air permeable layer with a porous or foam-based structure and at least one layer comprising activated carbon,
wherein the air permeable layer forms an outer layer of the wound dressing and wherein the wound dressing is adapted to be applied to a wound with the air permeable layer arranged on a side of the wound dressing facing the wound,
wherein the air permeable layer is formed by a hydrocolloid foam wherein the hydrocolloid is collagen,
wherein the air permeable layer has a compressive hardness in the range from 5 to 50 kPa,
wherein the activated carbon comprises granular activated carbon, and
wherein the activated carbon has a micropore volume content formed of micropores with pore diameters of ≤20 Å in the range from 60% to 95%, based on the total pore volume of the activated carbon.

3. A wound dressing for therapeutic wound care,
wherein the wound dressing has a multilayer structure, wherein the multilayer structure comprises at least one air permeable layer with a porous or foam-based structure and at least one layer comprising activated carbon,
wherein the air permeable layer forms an outer layer of the wound dressing and wherein the wound dressing is adapted to be applied to a wound with the air permeable layer arranged on a side of the wound dressing facing the wound,
wherein the air permeable layer is formed by a hydrocolloid foam wherein the hydrocolloid is collagen,
wherein the air permeable layer has a compressive hardness in the range from 5 to 50 kPa,
wherein the activated carbon comprises granular activated carbon,
wherein the activated carbon has a micropore volume content formed of micropores with pore diameters of ≤20 Å in the range from 60% to 95%, based on the total pore volume of the activated carbon, and
wherein the activated carbon has a biocidal, biostatic or antimicrobial effect, wherein the biocidal, biostatic or antimicrobial effect of the activated carbon is achieved through the production process of the activated carbon or through treatment of the activated carbon with at least one biocidal, biostatic or antimicrobial active substance.

\* \* \* \* \*